(12) United States Patent
Wright et al.

(10) Patent No.: US 10,048,185 B2
(45) Date of Patent: Aug. 14, 2018

(54) SYSTEMS, METHODS, AND APPARATUSES FOR MONITORING AND/OR CONTROLLING THE DENSITY OF A FLUID

(71) Applicant: PARASTIX, LLC, Newport News, VA (US)

(72) Inventors: David D. Wright, Vershire, VT (US); James H. Vogeley, Yorktown, VA (US); Taylor D. McClenny, Courtland, VA (US); Peter R. Merrick, Kilmarnock, VA (US); Paul A. Robinson, Norfolk, VA (US)

(73) Assignee: Parasitx, LLC, Newport News, VA (US)

( * ) Notice: Subject to any disclaimer, the term of this patent is extended or adjusted under 35 U.S.C. 154(b) by 77 days.

(21) Appl. No.: 15/027,687

(22) PCT Filed: Oct. 9, 2014

(86) PCT No.: PCT/US2014/059948
§ 371 (c)(1),
(2) Date: Apr. 6, 2016

(87) PCT Pub. No.: WO2015/054524
PCT Pub. Date: Apr. 16, 2015

(65) Prior Publication Data
US 2016/0252440 A1 Sep. 1, 2016

Related U.S. Application Data

(60) Provisional application No. 61/961,213, filed on Oct. 9, 2013.

(51) Int. Cl.
*G01N 9/00* (2006.01)
*G01N 9/02* (2006.01)
(Continued)

(52) U.S. Cl.
CPC .............. *G01N 9/002* (2013.01); *G01N 9/02* (2013.01); *G01N 9/10* (2013.01); *G01N 2009/024* (2013.01)

(58) Field of Classification Search
CPC ............ G01N 9/00; G01N 9/002; G01N 9/02; G01N 9/08; G01N 9/10; G01N 9/12; G01N 9/18; G01N 2009/024
See application file for complete search history.

(56) References Cited

U.S. PATENT DOCUMENTS 2,688,868 A * 9/1954 Elkins ..................... G01N 9/04
73/453
2,722,838 A * 11/1955 Vick Roy ................ G01N 9/10
73/451
(Continued)

FOREIGN PATENT DOCUMENTS

DE 700314 12/1940
DE 1943214 3/1971
(Continued)

OTHER PUBLICATIONS

"Uber fridge: controlling beer fermentation temperature from a web interface" Jacobs (Feb. 16, 2012), retrieved from http://www.elcojacobs.com/uberfridge-the-first-results-are-in/ (posted Feb. 16, 2012).

*Primary Examiner* — Nguyen Ha
(74) *Attorney, Agent, or Firm* — Shaddock Law Group, PC

(57) ABSTRACT

A density meter for measuring the density of a fluid, having a base plate, wherein a spring element is clamped to the base plate; a torpedo, wherein the torpedo comprises a known weight, and wherein the torpedo is attached or coupled to the
(Continued)

spring element; and a sensor, wherein the sensor measures a deflection of the spring element, as the torpedo displaces a volume of fluid.

19 Claims, 27 Drawing Sheets

(51) Int. Cl.
*G01N 9/12* (2006.01)
*G01N 9/18* (2006.01)
*G01N 9/10* (2006.01)

(56) References Cited

U.S. PATENT DOCUMENTS

| | | | | |
|---|---|---|---|---|
| 3,071,971 | A * | 1/1963 | Wallace | G01N 9/18 |
| | | | | 73/451 |
| 3,754,446 | A | 8/1973 | O'Connor | |
| 3,952,761 | A * | 4/1976 | Friedland | G01N 9/18 |
| | | | | 137/91 |
| 4,813,283 | A * | 3/1989 | Craubner | G01N 9/08 |
| | | | | 73/436 |
| 5,614,672 | A | 3/1997 | Legendre et al. | |
| 6,380,499 | B1 | 4/2002 | Edwards | |
| 2002/0033356 | A1 * | 3/2002 | Honda | B01D 17/0208 |
| | | | | 208/251 R |
| 2014/0260607 | A1 * | 9/2014 | Baron | G01N 9/16 |
| | | | | 73/448 |

FOREIGN PATENT DOCUMENTS

| | | | | |
|---|---|---|---|---|
| FR | 2128956 | | 10/1972 | |
| WO | WO 8901618 A1 * | | 2/1989 | G01N 9/10 |

\* cited by examiner

SYSTEMS, METHODS, AND APPARATUSES FOR MONITORING AND/OR CONTROLLING THE DENSITY OF A FLUID

CROSS-REFERENCE TO RELATED APPLICATIONS

This patent application claims the benefit of U.S. Patent Application Ser. No. 61/961,213, filed Oct. 9, 2013, the entire disclosure of which is incorporated herein by reference.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

NOTICE OF COPYRIGHTED MATERIAL

The disclosure of this patent document contains material that is subject to copyright protection. The copyright owner has no objection to the reproduction by anyone of the patent document or the patent disclosure, as it appears in the Patent and Trademark Office patent file or records, but otherwise reserves all copyright rights whatsoever. Unless otherwise noted, all trademarks and service marks identified herein are owned by the applicant.

BACKGROUND OF THE INVENTION

1. Field of the Invention

The present disclosure relates generally to the fields of the measurement of the density of a fluid, and computer applications. More specifically, the present invention relates to an density meter adaptable to be used to provide continuous real-time measurement of the density of a fluid, particularly to the measurement taken via electronic means, the signal processing of the measurement to provide detailed information and computer applications, mobile computer applications, tablet applications, or smart phone applications for collecting transmitted raw data, correlating the collected data, and displaying the results of the correlated data regarding the density of a fluid periodically or historically.

2. Description of Related Art

Typically, density measurements of a fluid are performed using a hydrometer. However, depending on the application, density may be reported as specific gravity, which is the density ratio of the fluid to a reference fluid, such as water. Alternative scales related to concentration of, for instance, sugar, in the fluid such as Plato or Brix or other scale such as Balling or Baume may be used.

Devices generally classified as hydrometers determine density by several methods including flotation, direct measurement of mass and volume, and weight of fluid displaced by a submerged object. The most common type of hydrometer is a glass tube with a weight at one end and a series of scales at the other. The hydrometer floats in a fluid so that the density can be read by viewing where the bottom of the meniscus of the fluid appears in relation to the hydrometer's scale.

Because sugar is more dense than water, a hydrometer will float higher in a fluid with a high degree of sugar. Conversely, because alcohol is less dense than water, a hydrometer will float lower in a fluid with a higher alcohol content.

In order to measure the density of a fluid, a sample of the fluid is typically removed from the main body of fluid to be tested and placed in a separate container for testing. Then, a hydrometer is lowered into the fluid in the test container and the density is measured visually by identifying where the bottom of the meniscus is around the hydrometer. The test fluid cannot be placed back into the main fluid, but must be discarded.

Once the density measurement is made, the measurement must be corrected for temperature differentiation.

Each time the fermenter is opened, it is possible for bacteria to be introduced into the fluid. Therefore, because the seal on the fermenter must be broken each time a test sample is removed, because each test sample must be discarded after use, and for other reasons, it is impractical to make more than a few measurements during the fermentation or brewing process. The first measurement is typically taken to determine the initial, starting density of the unfermented fluid, prior to the addition of any yeast to the fluid. This measurement will be necessary in order to determine the alcohol content of the final fluid.

The next measurement is not typically taken until it is believed that the fluid is near the end of the fermentation process. The measurements taken at this point are typically used as a gauge of the fermentation process and to signal when the fluid may be ready for bottling.

The third measurement is typically taken when it is believed that the fermentation process is complete. This provides a final density, which will be used to determine the final alcohol content of the fluid. Generally, another measurement is taken about a day later. If the result of this measurement is lower than the result of the third measurement, the fermentation process is not complete and the fluid is allowed to continue the fermentation process for another day or two. If the fluid is bottled before it is done fermenting, it may over carbonating as it finishes the fermentation process inside the bottle.

If the results of this measurement and the third measurement are the same, most of the sugar in the fluid has been turned into alcohol, and the fluid can be bottled.

By subtracting the result of the initial density measurement from the result of the final density measurement (at bottling), and multiplying the result by 131, the percentage of alcohol content of the fluid is determined.

The above is merely one example of the related art and it should be understood that the invention contemplated herein can be utilized to produce density measurements of any fluid application.

Any discussion of documents, acts, materials, devices, articles, or the like, which has been included in the present specification is not to be taken as an admission that any or all of these matters form part of the prior art base or were common general knowledge in the field relevant to the present disclosure as it existed before the priority date of each claim of this application.

BRIEF SUMMARY OF THE INVENTION

However, the typical hydrometer arrangements and the current methods for measuring, monitoring, and controlling a fluid during the fermentation process have various shortcomings. To overcome these shortcomings, the systems, methods, and apparatuses of the current invention provide real-time monitoring, measurement, and control of a fluid, thereby helping to ensure proper fermentation of a fluid and consistency from batch to batch.

Hydrometers are used in the laboratory to measure density electronically, typically by weighing a fixed volume of fluid with an electronic weight scale or measuring the change in weight as an object is submerged. One limitation of using a laboratory device to measure the density during fermentation is, as discussed above, the need to break the seal. Breaking the seal during the fermentation process of beer, wine, or other substance to take a sample and make a hydrometer reading can lead to contamination of the brew. A device of the present invention overcomes this limitation.

This invention pertains to the continuous real-time measurement of the density of a fluid, and particularly to the measurement taken via electronic means, and the signal processing of the measurement to provide detailed information of the fermentation process. For descriptive purposes, the systems, methods, and apparatuses of the present invention are described with reference to the density of fluids such as beer or wine, wherein measurement of density in such cases indicates the degree of completion of fermentation and the alcohol content. However, it should be appreciated that these are merely exemplary and not limiting or exclusive applications of the present invention. Thus, the systems, methods, and apparatuses of the present invention may be applied to any fluid in which it is preferable to accurately measure and/or control the density and/or temperature over time.

The present invention is a continuous reading density meter that is at least partially contained within the sealed fermentation volume and which is capable of locally storing in memory and/or transmitting density readings to a secondary device or devices at a selected scheduling interval by means of wireless communication or through a tethered signal line. The readings can be viewed or stored electronically. The volume of the object submerged in the fluid, herein called a torpedo, and other calibration factors are stored in the density meter to let density be calculated from the measurement of the torpedo weight.

In various exemplary, non-limiting embodiments, as illustrated in certain of the drawing figures, during use, the torpedo may optionally be fully submerged below the surface of the fluid, avoiding "noise" or disturbance from bodies collecting on the fluid's surface and external environments. Alternatively, the torpedo may optionally be partially submerged below the surface of the fluid.

In various exemplary, non-limiting embodiments, the systems, methods, and apparatuses of the present invention (hereinafter sometimes referred to as the "BeerBug™ Application" and/or the "BeerBug™ App") provide an application that can be accessed by a user. The BeerBug™ App automatically retrieves updated and/or real-time density data from a network and presents visual representations of pertinent data in graphs and metrics. From this visual representation, users can quickly and easily ascertain the current density of a fluid, as well as historical density information for the fluid and the direction of the density trend.

In various exemplary, nonlimiting embodiments, the BeerBug™ App has a method for displaying historical density data, a current density, and potentially a density trend for a fluid. In various exemplary embodiments, the BeerBug™ App method includes at least the ability to collect density data and transmit the collected density data. The BeerBug™ App method also includes at least some of receiving the transmitted density data; associating the collecting density data with a discrete user; filtering the collected density data to produce filtered density data; and storing the collected and filtered density data in a database such that the collected and filtered density data is associated with the discrete user.

The BeerBug™ App method also includes at least some of receiving a query regarding density data from a discrete user; retrieving, in response to the query, density data associated with the queried discrete user; transmitting the retrieved density data associated with the query to a client device; allowing the transmitted density data to be received by the client device; controlling the client device to convert the received density data into a graphical representation of the density data; and controlling the client device to display the graphical representation in a manner so as to represent the historical and current filtered density data. The BeerBug™ App method also includes at least some of automatically sending messages via the Internet to users based on the measurements and/or derived products (as further defined herein). Users can receive messages on computers, cell phones, tablets, etc., via wired, cell, Wi-Fi, Bluetooth, or other known or later developed connections.

In various exemplary, nonlimiting embodiments, the BeerBug™ App also includes a unique graphical user interface or display that provides density or density trend information in a unique, user-friendly way. The BeerBug™ App provides information to a user that does not require the user to continuously interact with a fluid in order to receive updated information regarding the density of the fluid.

In various exemplary, nonlimiting embodiments, the BeerBug™ App also includes at least some of receiving current temperature data representing a temperature of a fluid; comparing the current temperature data to a desired temperature data with in a database; and controlling a heating and/or cooling means, if the current temperature of the fluid is not equal to the desired temperature, to alter the temperature of the fluid until a subsequent temperature of the fluid is equal to the desired temperature.

The systems, methods, and apparatuses of the present invention can be utilized in a number of varying applications. For example, the systems, methods, and apparatuses of the present invention may be utilized as a fermentation hydrometer and thermometer in beer making and wine making. Density measurements of the prior art in brewing beer are invasive. The seal on the brew is broken and a sample is withdrawn to measure sugar content using a hydrometer or a refractometer. The device of the present invention is a major improvement in that continuous readings are possible without interrupting the seal. Events such as yeast kick-off and end of active fermentation are clearly seen.

The systems, methods, and apparatuses of the present invention may be utilized in salinity reading for salt-water aquariums or swimming pools. One of the impediments to wider acceptance of salt-water aquariums is the difficulty of maintaining the salinity of the tank. A device of the present invention enables the salinity of a salt-water aquarium to be captured by general purpose computers so that the salinity can be controlled automatically.

The systems, methods, and apparatuses of the present invention may also be utilized in other applications where density, specific gravity, and/or temperature measurements are useful in mediums such as, for example, alcohol, beer, wine, cider, spirits, and others, water, petroleum, cooking, consumption, or other oils, acid, vinegar, battery acids and/or electrolytes, fruit juices, and other fluids.

The systems, methods, and apparatuses of the present invention may be utilized in boiling maple syrup to a particular sugar content.

The systems, methods, and apparatuses of the present invention may be utilized in the measurement of the density of a slurry in an industrial process such as papermaking. Measurement of the density of a mixture such as battery acid.

Accordingly, the presently disclosed invention provides systems, methods, and apparatuses that provide real-time monitoring, measurement, and control of a fluid.

The presently disclosed invention separately provides a novel hydrometer assembly that determines density by monitoring the weight of fluid displaced by a submerged object.

The presently disclosed invention separately provides systems, methods, and apparatuses that monitor and the fermentation process.

The presently disclosed invention separately provides systems, methods, and apparatuses that may be utilized to control the fermentation process.

The presently disclosed invention separately provides systems, methods, and apparatuses that may be utilized to control the temperature of a fluid.

The presently disclosed invention separately provides systems, methods, and apparatuses that are capable of providing information regarding whether the yeast has started fermenting in a fluid.

The presently disclosed invention separately provides systems, methods, and apparatuses that are capable of providing information regarding whether the fermentation process is actually completed in a fluid.

The presently disclosed invention separately provides systems, methods, and apparatuses that may be utilized to ensure proper fermentation of a fluid and consistency from batch to batch.

The presently disclosed invention separately provides systems, methods, and apparatuses that may be utilized to measure a fluid's change in density.

The presently disclosed invention separately provides systems, methods, and apparatuses that may be utilized to measure and display a fluid's change in density over time and higher order derivatives of the change in density over time.

The presently disclosed invention separately provides systems, methods, and apparatuses that can provide information regarding the status of a fluid to a remote location.

The presently disclosed invention separately provides systems, methods, and apparatuses that can provide information regarding the status of a fluid via the Internet and/or an Internet webpage.

The presently disclosed invention separately provides systems, methods, and apparatuses that can provide information regarding the status of a fluid via a mobile application.

The presently disclosed invention separately provides a density meter that can be easily operated by a user.

The presently disclosed invention separately provides a BeerBug™ App that provides a visual display of the density of a fluid that can be easily visually determined by a user.

The presently disclosed invention separately provides a BeerBug™ App that provides updated and/or real-time density data to a user.

The presently disclosed invention separately provides a BeerBug™ App that can operate to control the fermentation process of a fluid.

These and other aspects, features, and advantages of the present invention are described in or are apparent from the following detailed description of the exemplary, non-limiting embodiments of the present invention and the accompanying figures. Other aspects and features of embodiments of the present invention will become apparent to those of ordinary skill in the art upon reviewing the following description of specific, exemplary embodiments of the present invention in concert with the figures. While features of the present invention may be discussed relative to certain embodiments and figures, all embodiments of the present invention can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present invention.

Any benefits, advantages, or fluids to problems that are described herein with regard to specific embodiments are not intended to be construed as a critical, required, or essential feature(s) or element(s) of the present invention or the claims.

BRIEF DESCRIPTION OF THE SEVERAL VIEWS OF THE DRAWINGS

As required, detailed exemplary embodiments of the present invention are disclosed herein; however, it is to be understood that the disclosed embodiments are merely exemplary of the invention that may be embodied in various and alternative forms, within the scope of the present invention. The figures are not necessarily to scale; some features may be exaggerated or minimized to illustrate details of particular components. Therefore, specific structural and functional details disclosed herein are not to be interpreted as limiting, but merely as a basis for the claims and as a representative basis for teaching one skilled in the art to employ the present invention.

The exemplary embodiments of this invention will be described in detail, with reference to the following figures, wherein like reference numerals refer to like parts throughout the several views, and wherein.

DETAILED DESCRIPTION OF THE INVENTION

Figure 1A:
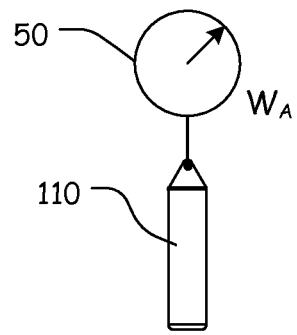
FIG. 1A illustrates the operating principals of a first exemplary embodiment of the density meter, according to this invention.

For simplicity and clarification, the design factors and operating principles of the density meter according to this invention are explained with reference to various exemplary embodiments of a density meter according to this invention. The basic explanation of the design factors and operating principles of the systems, methods, and apparatuses of the present invention is applicable for the understanding, design, and operation of the systems, methods, and apparatuses of this invention. It should be appreciated that the density meter can be adapted to many applications where a density meter can be used.

As used herein, the word "may" is meant to convey a permissive sense (i.e., meaning "having the potential to"), rather than a mandatory sense (i.e., meaning "must"). Unless stated otherwise, terms such as "first" and "second" are used to arbitrarily distinguish between the elements such terms describe. Thus, these terms are not necessarily intended to indicate temporal or other prioritization of such elements.

The term "coupled", as used herein, is defined as connected, although not necessarily directly, and not necessarily mechanically. The terms "a" and "an" are defined as one or more unless stated otherwise.

Throughout this application, the terms "comprise" (and any form of comprise, such as "comprises" and "comprising"), "have" (and any form of have, such as "has" and "having"), "include", (and any form of include, such as "includes" and "including") and "contain" (and any form of contain, such as "contains" and "containing") are used as open-ended linking verbs. It will be understood that these terms are meant to imply the inclusion of a stated element, integer, step, or group of elements, integers, or steps, but not the exclusion of any other element, integer, step, or group of elements, integers, or steps. As a result, a system, method, or apparatus that "comprises", "has", "includes", or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

It should also be appreciated that throughout this application the terms "density meter", "torpedo", "beer", and "wine" are used for basic explanation and understanding of the operation of the systems, methods, and apparatuses of this invention. Therefore, the terms "density meter", "torpedo", "beer", and "wine" are not to be construed as limiting the systems, methods, and apparatuses of this invention. Thus, for example, the term "torpedo" is to be understood to broadly include any portion of material having a known weight.

For simplicity and clarification, the systems, methods, and apparatuses of this invention will be described as being used in conjunction with the fermentation of beer or wine. However, it should be appreciated that these are merely exemplary embodiments of the systems, methods, and apparatuses of the present invention and are not to be construed as limiting this invention. Thus, the systems, methods, and apparatuses of this invention may be utilized in conjunction with any fluid in which the density and/or temperature needs to be accurately measured and/or controlled over time.

Similarly, for simplicity and clarification, the BeerBug™ App of this invention will be described as being used as a mobile application. However, it should be appreciated that these are merely exemplary embodiments of the BeerBug™ App and are not to be construed as limiting this invention. Thus, the BeerBug™ App of this invention may be utilized in conjunction with alternate applications and with other devices, such as, for example, an interactive website.

In the following description, for purposes of explanation and not limitation, specific details are set forth such as particular architectures, interfaces, techniques, etc. in order to provide a thorough understanding of the present invention. However, it will be apparent to those skilled in the art that the present invention may be practiced in other embodiments that depart from these specific details. That is, those skilled in the art will be able to devise various arrangements that, although not explicitly described or shown herein, embody the principles of the invention and are included within its spirit and scope. In some instances, detailed descriptions of well-known devices, circuits, and methods are omitted so as not to obscure the description of the present invention with unnecessary detail. All statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The technology disclosed herein concerns method and apparatus whereby a precise measurement of density may be acquired, stored, and/or reported by a self-contained hydrometer device. As used herein, "density" is used as the example fluidic physical property; however the device measurement also applies generally to the characteristic of fluid density.

Figure 1B:
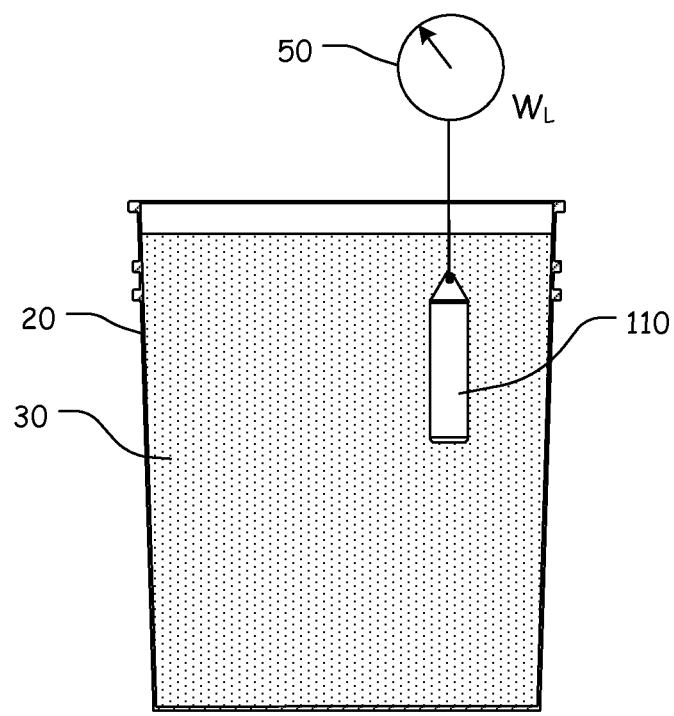
FIG. 1B illustrates the operating principals of a first exemplary embodiment of the density meter, according to this invention.

Turning now to the drawing FIGS., FIGS. 1-20 illustrate certain elements and/or aspects of various exemplary embodiments of the systems, methods, and apparatuses of this invention. As illustrated most clearly in FIG. 1A, the torpedo 110 has a weight in air, $W_A$, and, as illustrated most clearly in FIG. 1B, a weight in fluid, $W_L$. The weight sensor 50 may be a strain gage instrumented beam such as is used in weighing scales, or sensing of the deflection of a spring element via capacitive, optical, or inductive means, or other type of transducer. The basic relationships among the measured variables and density are defined in FIGS. 1A-1B.

The torpedo 110 is used to determine the density of the fluid 30 by the principle of Archimedes. As represented by the equations below, the difference in the weight of the torpedo 110 in air and in fluid 30 equals the product of the volume of the object times the difference of density between fluid and air.

The density of air, the volume of the object, the weight in air, $W_A$, and a weight in fluid, $W_L$, are measured so the density, $\rho$, of the fluid 30 can be calculated. The density meter 100 accomplishes this measurement through use of the torpedo 110 with known volume and a suitable weighing means.

$$(\rho_L - \rho_A)V = W_A - W_L \text{ or } W_A + \rho_A V = W_L + \rho_L V$$

Then:

$$\text{Density} = (W_A + \rho_A V - W_L)/(\rho_W V)$$

A=Air
L=Fluid
W=Water
$\rho$=Density
V=Volume
W=Weight

Figure 2A:
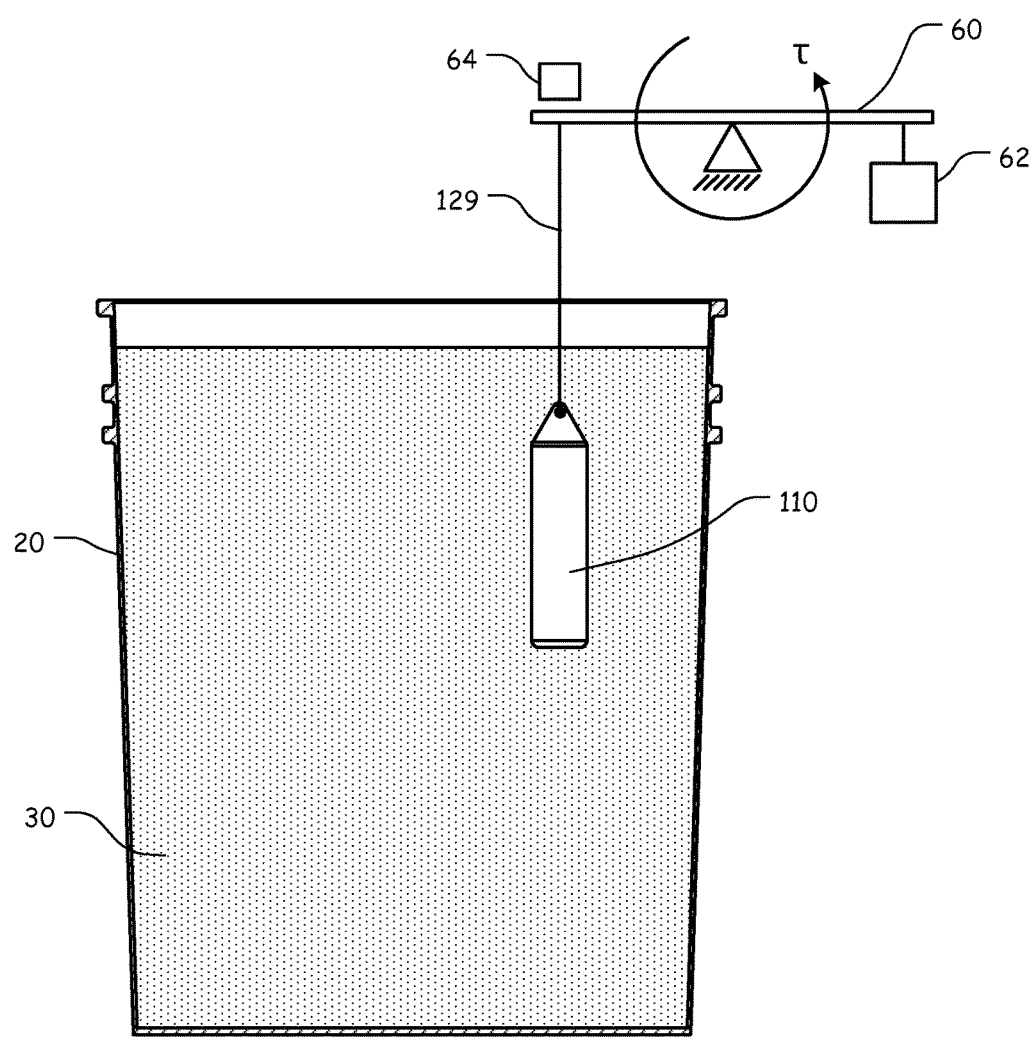
FIG. 2A shows the measurement of torpedo weight as the position of a rigid counterbalanced beam with torsion spring element, according to this invention.
Figure 2B:
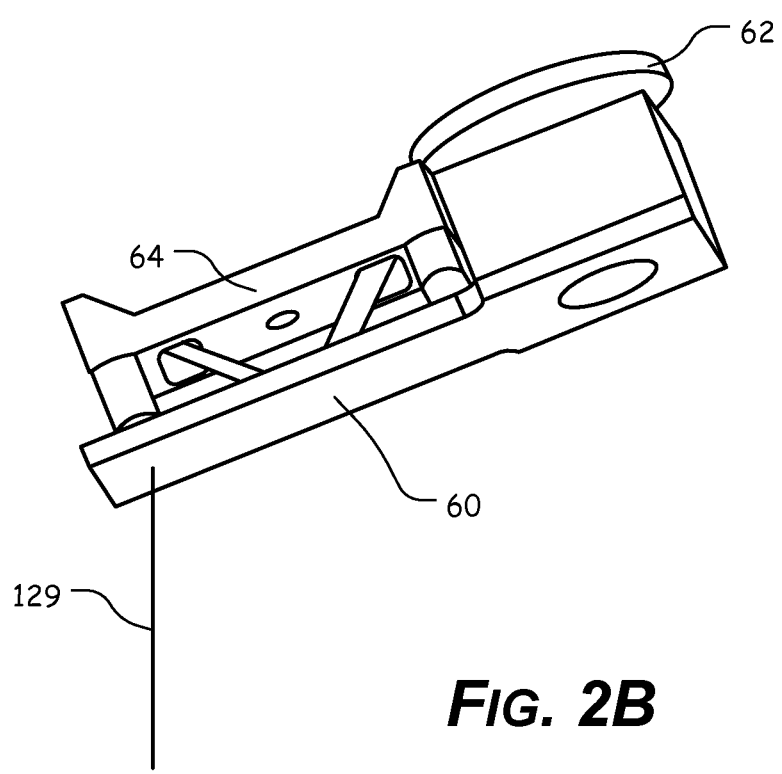
FIG. 2B shows a first exemplary embodiment of a torque mount measurement device, according to this invention.
Figure 3:
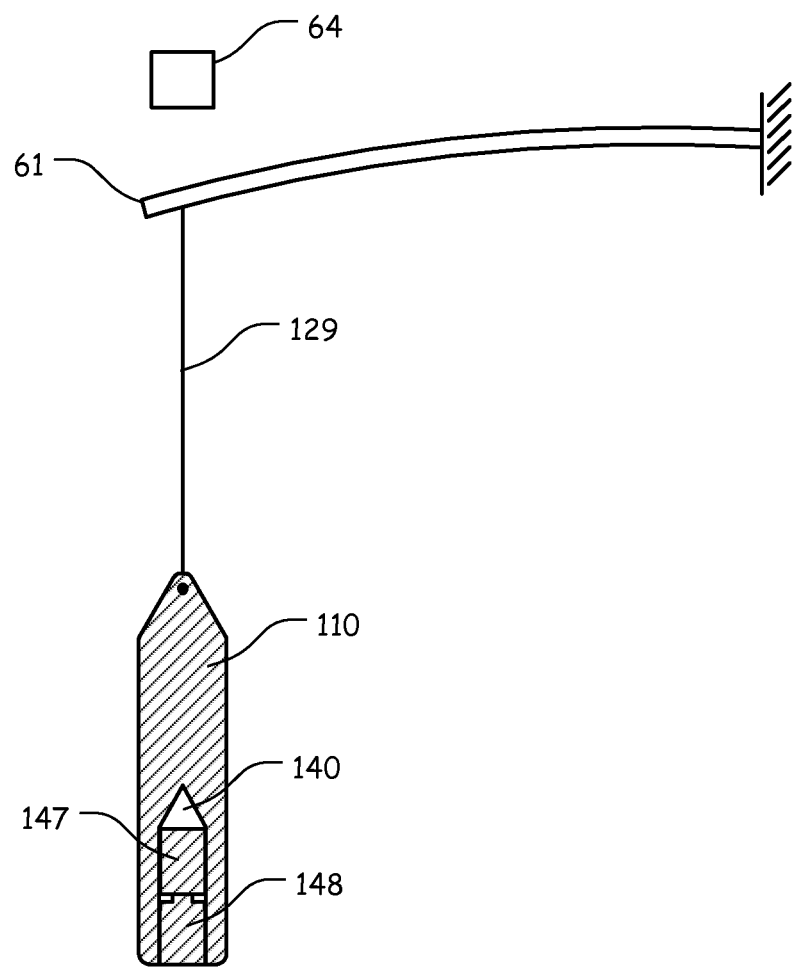
FIG. 3 shows how the torpedo may be weighted to achieve the same effect as counterbalancing, according to this invention.
Figure 4:
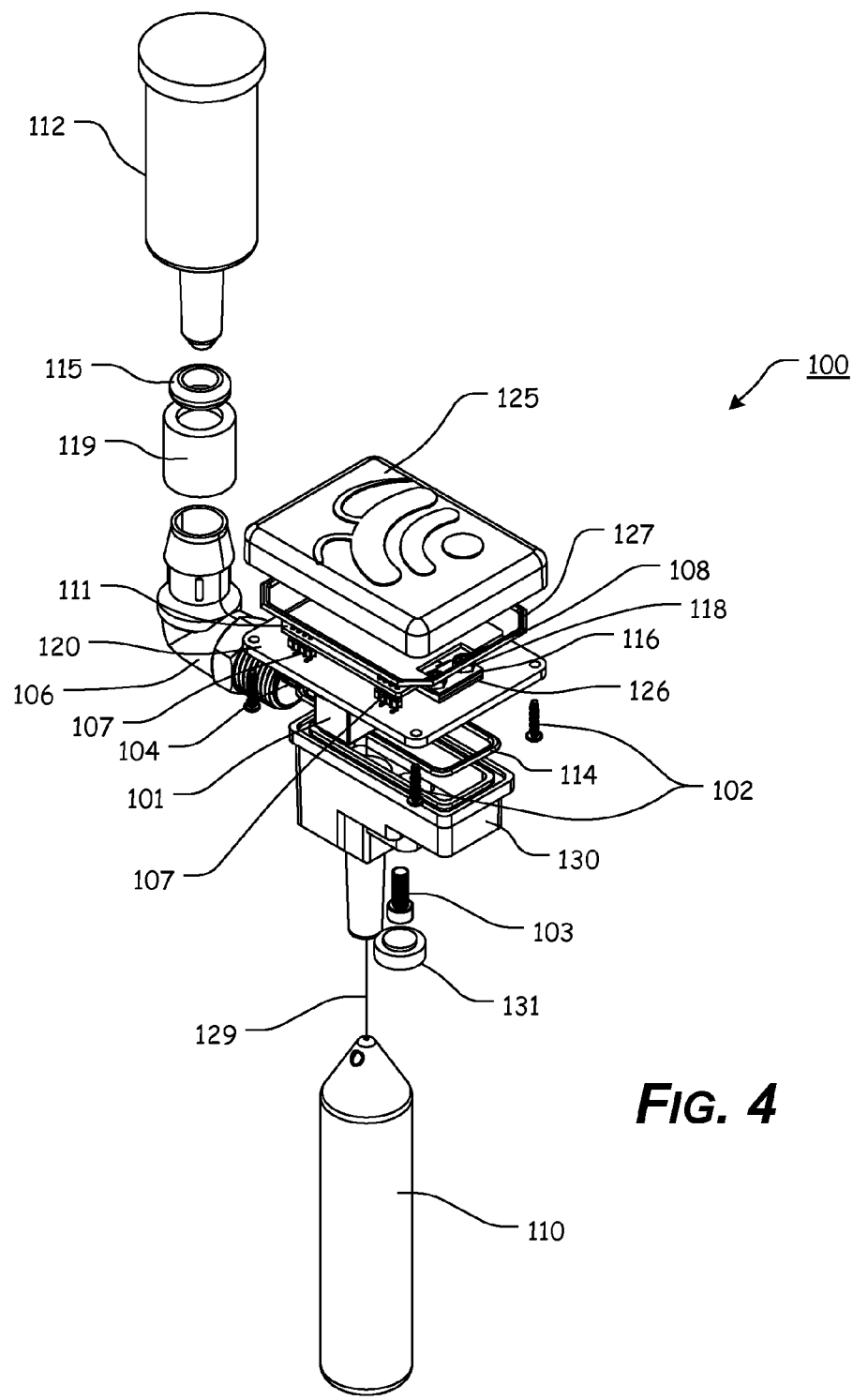
FIG. 4 shows an upper exploded view of a first exemplary embodiment of the density meter, according to this invention.

FIGS. 2 and 3 describe the sensing in more detail. The rigid beam 60, of FIG. 2A, is mounted on flexures, which both create a low friction pivot and a torsional return spring element. A counterbalance weight 62 balances the rigid beam 60 at the center of the anticipated density range. The torsional spring element provides a torque, $\tau$, in proportion to the rigid beam 60 deflection and hence in proportion to the differential weight between the submerged rigid beam 60 and the counterbalance weight 62. The counterbalance weight 62 allows a compliant torsional spring element to be used while limiting the deflection of the rigid beam 60 to a practical range for the sensor 64. FIG. 2B shows an alternative way to implement the device of the present invention.

FIG. 3 shows a cantilever beam 61, whose deflection depends on the weight of a submerged torpedo 110. This implementation is similar to the counterbalance beam 60 of FIG. 2A with no counter weight. The cantilever beam 61 in FIG. 3 is intended to deflect rather than being rigid; its deflection is a measure of the weight of the submerged torpedo 110.

In this embodiment, a counterbalance effect is achieved by modifying the torpedo 110 as shown in the cross-sectional view of the torpedo 110 in FIG. 3. In various exemplary embodiments, the main body of the torpedo 110 comprises food grade HDPE, which is lighter than fluid 30. However, by hollowing out a section of the torpedo 110 to form a cavity 140 and positioning a weighted slug 147 within the cavity 140. A cap or plug 148 is used to secure the weighted slug 147 within the cavity 140. The weighted slug 147 comprises a substantially heavy material that possesses a known weight. In this manner, the submerged weight of the torpedo 110 can be made to be heavier than the fluids of interest over a suitable range of specific gravities.

If a heavier than water material, such as glass or Teflon is used to form the body of the torpedo 110, the same counterbalance effect may be achieved by filling the cavity 140 with a gas. It is imperative to add (or subtract) the added weight in such a way that the center of gravity of the torpedo 110 is below the center of buoyancy.

In various exemplary, nonlimiting embodiments, food grade materials such as HDPE are used for the torpedo 110, which is submerged in the fluid 30. Other housing/body materials may be incorporated depending on the usage environments such as Teflon or glass. Food grade Viton or other food grade rubber can be used for sealing the hydrometer housing 130 from the fermentation environment.

FIGS. 4-7 show various exploded views of a first exemplary embodiment of the density meter 100, of the present invention. As shown in FIGS. 4-7, the density meter 100 comprises at least some of a modular jack 101, attachment screws 102, a screw 103, a USB port 104, a screw 105, an elbow 106, headers 107, a sensing beam 108, screws 109, a torpedo 110, a printed circuit board 111, a bubbler 112, a spring element or deflecting load beam 113, a housing seal 114, a grommet 115, an upper wedge 116, screws 117 and corresponding nuts 118, an elbow cap 119, a base plate 120, clamps 121, magnets 122, a snap 123, a bridge 124, a cover 125, a bottom wage 126, a cover seal 127, a retaining washer 128, a suspension line 129, a housing 130, a knob 131, a temperature sensor 132, and an optional heating and/or cooling means 133.

In various exemplary embodiments, the modular jack 101 is electronically coupled to the printed circuit board 111 and provides the density meter 100 with a hardwired connection, such that the density meter 100 can be connected to a network in order to be programmed, reprogrammed, or to transmit and/or receive data.

The USB port 104 is also electronically coupled to the printed circuit board 111 and also provides the density meter 100 with a hardwired connection, such that the density meter 100 can be connected to a network in order to be programmed, reprogrammed, or to transmit and/or receive data.

It should also be appreciated that a more detailed explanation of the specific components or elements used for the modular jack 101 and/or the USB port 104, instructions regarding how to use the modular jack 101 and/or the USB port 104, methods for using the modular jack 101 and/or the USB port 104 to connect with a network or transmit and/or receive data, and certain other items and/or techniques necessary for the implementation and/or operation of the modular jack 101 and/or the USB port 104 in connection with the elements of the present invention are not provided herein because such elements are commercially available and/or such background information will be known. Therefore, it is believed that the level of description provided herein is sufficient to enable one of ordinary skill in the art to understand and practice the invention as described.

Each also be appreciated that the bubbler 112, the grommet 115, the elbow cap 119, and the elbow 106 are known elements that will be familiar to one of ordinary skill in the art.

The headers 107 provide electrical connection between the base plate 120 and the printed circuit board 111.

The torpedo 110, having a known weight, is suspended from the spring element or deflecting load beam 113, by a suitable suspension line 129. The deflecting load beam 113 is attached or coupled, such as, for example, by clamps 121, to the base plate 120, which also holds the electronics necessary to operate the density meter 100 and the printed circuit board 111, and the cover 125.

In certain exemplary, nonlimiting embodiments, the deflecting load beam 113 is 0.012" thick and 0.375" wide and 1.22" long from clamp to attachment.

In certain exemplary, nonlimiting embodiments, the deflecting load beam 113 is formed from stainless steel, which is suitably hardened to serve as a spring element. In one variation, a portion of a circuit board is cut out to serve as a deflecting load beam. The base plate 120, is typically anodized aluminum, but may be advantageously be made from circuit board material such as FR4 or G10 and may incorporate the electronics and sensing electrode.

Figure 10A:
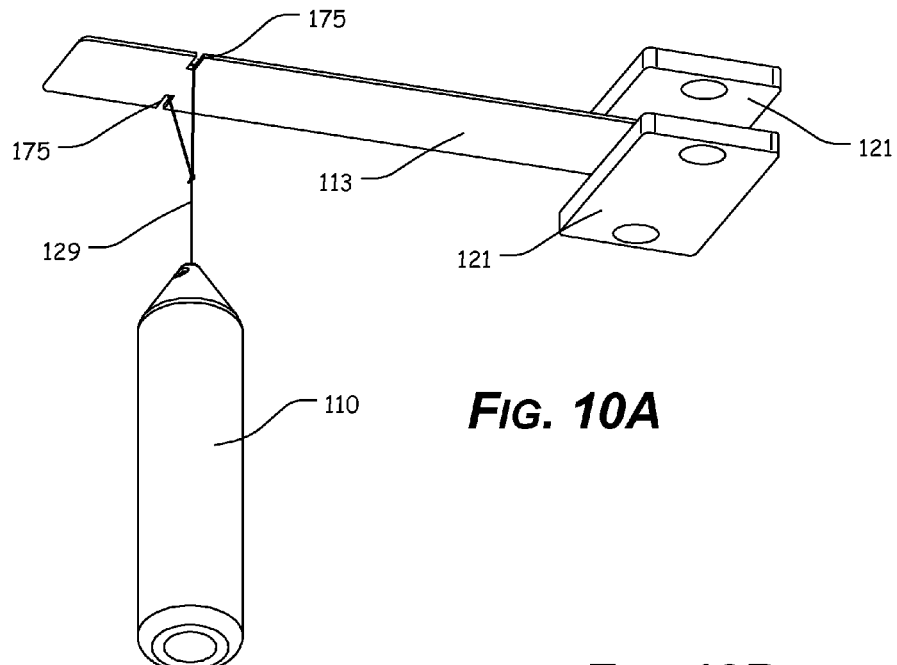
FIG. 10A shows an exemplary arrangement of a deflecting load beam, according to this invention.
Figure 10B:
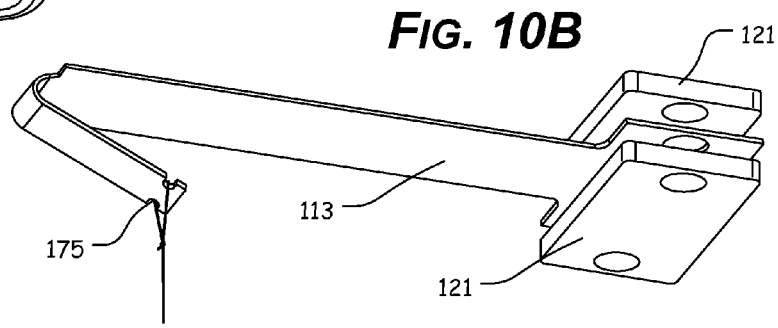
FIG. 10B shows an exemplary arrangement of a deflecting load beam, according to this invention.
Figures 10C, 10D, 10E:
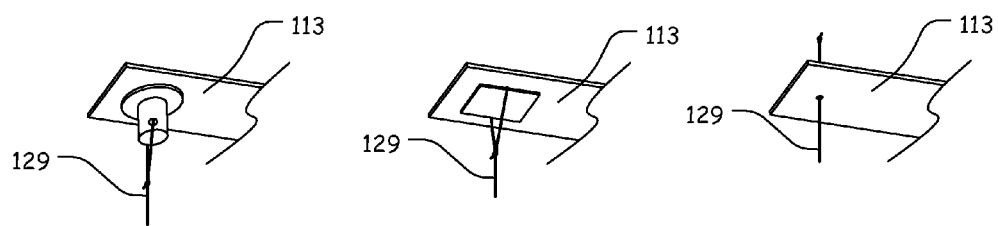
FIG. 10C shows an exemplary arrangement of a deflecting load beam, according to this invention.
FIG. 10D shows an exemplary arrangement of a deflecting load beam, according to this invention.
FIG. 10E shows an exemplary arrangement of a deflecting load beam, according to this invention.

Several variations in the deflecting load beam 113 shape and attachment are illustrated in FIG. 10A-E-FIG. 14. In the embodiment shown in FIG. 10a, the suspension line 129 attaches to the deflecting load beam 113 by tying using notches 175 in the deflecting load beam 113 to attach or coupled the suspension line 129, to torpedo 110. Alternatively, the suspension line 129 may be threaded through a hole in an attachment, as illustrated in FIG. 10c, or a loop, as illustrated in FIG. 10d.

As shown in FIG. 10b, the attachment and notches 175 may be formed by bending a tab from the material of the deflecting load beam 113.

FIG. 10e shows the suspension line 129 passing through a hole 176 in the deflecting load beam 113 with a stopper knot or attachment to prevent it pulling back through the hole and this has been preferred because of its simplicity.

Figure 11:
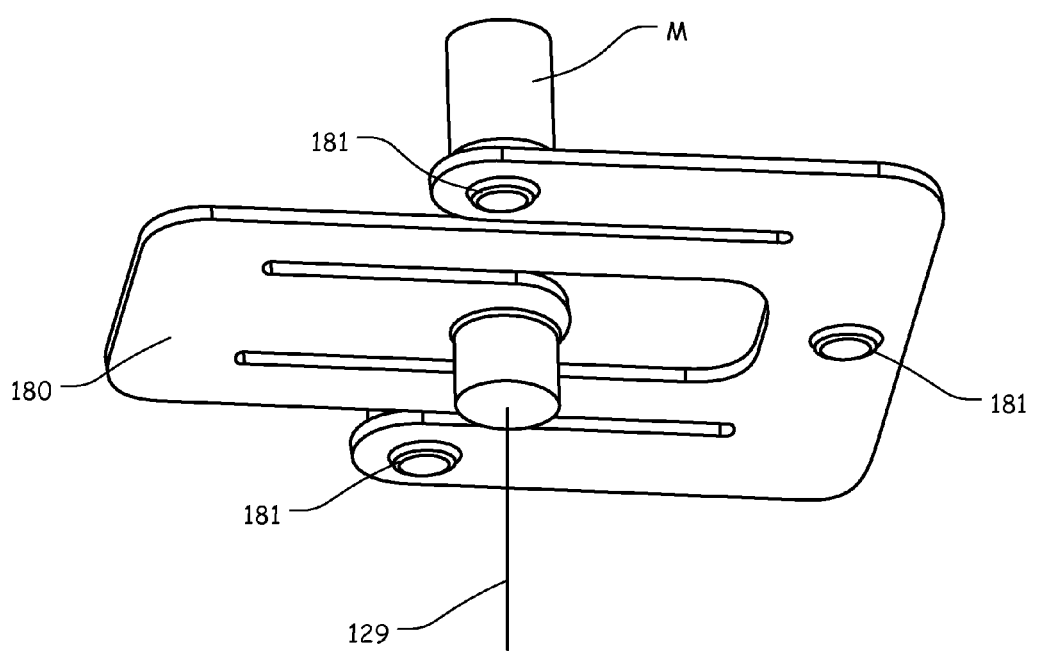
FIG. 11 shows an exemplary embodiment of a spring assembly having a spring element that remains parallel to a sensing electrode during its deflection by a torpedo weight, according to this invention.
Figure 12:
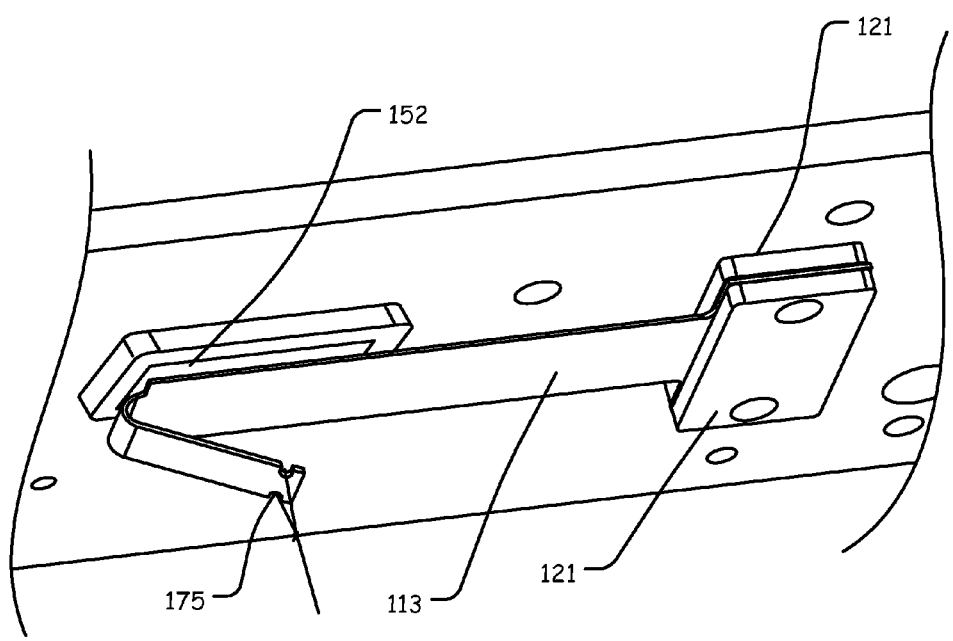
FIG. 12 shows a capacitive sensing means for beam deflection, according to this invention.

The alternative spring element 180, as illustrated in FIG. 11 is mounted to the base plate 120 at at least three mounting points 181. The spring element 180 is loaded by the attached suspension line 129. This type of spring element is slope compensated so that in the vicinity of the mounting points 181, the spring element 180 remains flat during deflection, which simplifies the displacement sensing.

Figure 14:
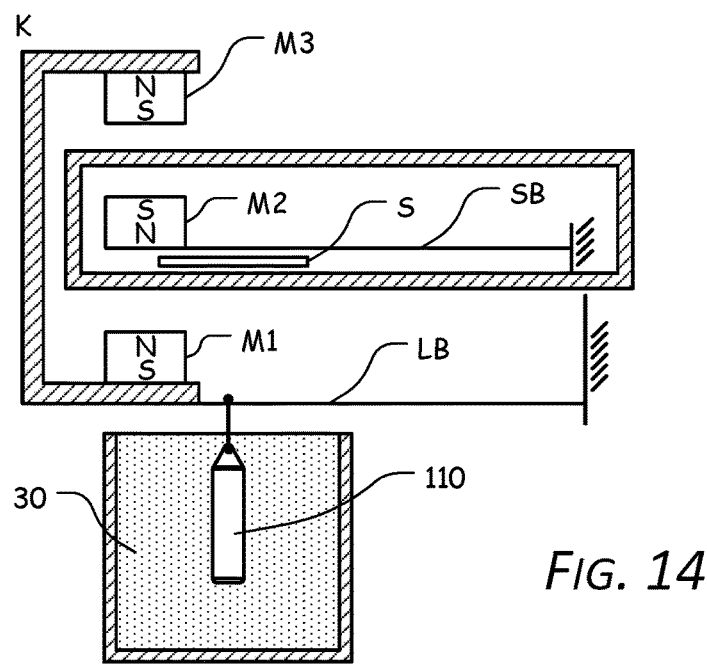
FIG. 14 shows a second alternate beam configuration, according to this invention.

The beam variations shown in FIG. 14 show isolation of the sensing beam 108 from the fluid 30 contiguous with the deflecting load beam 113. For instance, this method prevents condensation from influencing a capacitance sensor measurement.

Figure 13:
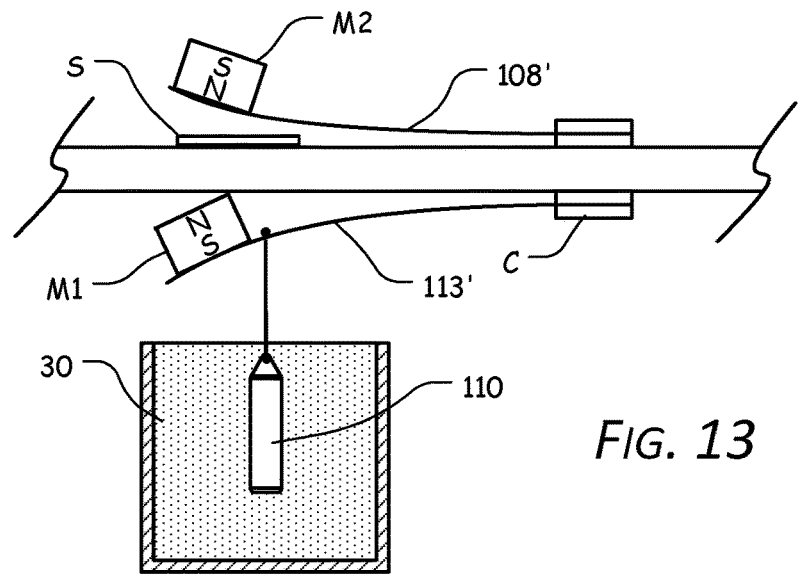
FIG. 13 shows a first alternate beam configuration, according to this invention.

In FIG. 13, the spring element is a deflecting load beam 113' and the deflecting load beam 113' is coupled to the sensing beam 108' such that movement of said deflecting load beam 113' is coupled to movement of said sensing beam 108'. In this embodiment, the sensing electrode S measures a capacitance between said sensing beam 108' and one or more sensing electrodes.

The deflections of the deflecting load beam 113' are communicated to the sensing beam 108' by the opposing magnetic fields of magnets M1 and M2. The deflecting load beam 113' is thicker and stiffer than the sensing beam 108' so that the sensing beam 108' essentially follows the deflection of the deflecting load beam 113'. The sensing beam 108' moves about half as far as the deflecting load beam 113' because of the change in magnetic field with distance relative to the stiffness of the sensing beam 108'.

In FIG. 14, the sensing beam 108 is mounted within a sealed enclosure and is held in place between the two magnets of the deflecting load beam 113. The two magnets, M1 and M3 are fixed relative to each other by a keeper, K, which may be a magnetically soft material such as 400 series stainless steel, thereby increasing the apparent strength of the magnets. Magnets M1 and M2 repel and this force is balanced by the repulsion between M2 and M3 so that the sensing beam 108 is essentially undeflected when there is no load on the deflecting load beam 113. As loads are applied by the torpedo 110, the sensing beam 108 follows the deflecting load beam 113 with only a slight lag due to the stiffness of the sensing beam 108.

The configuration shown in FIG. 14 has advantages over the configuration in FIG. 13. For example, as the strength of the magnets change due to, for instance, temperature coefficient of remanence, the sensing beam magnet M2 still stays centered between the magnets M1 and M3 on the deflecting load beam 113. A second advantage is a greater degree of deflection of the sensing beam 108 than the deflection that occurs in the two magnet configuration. A third advantage is that the magnetic forces and gradient of magnetic forces, which couple the sense and deflecting load beams 113 can be much greater in the three magnet configuration. The higher forces increase the ability to resist perturbations.

Figure 16:
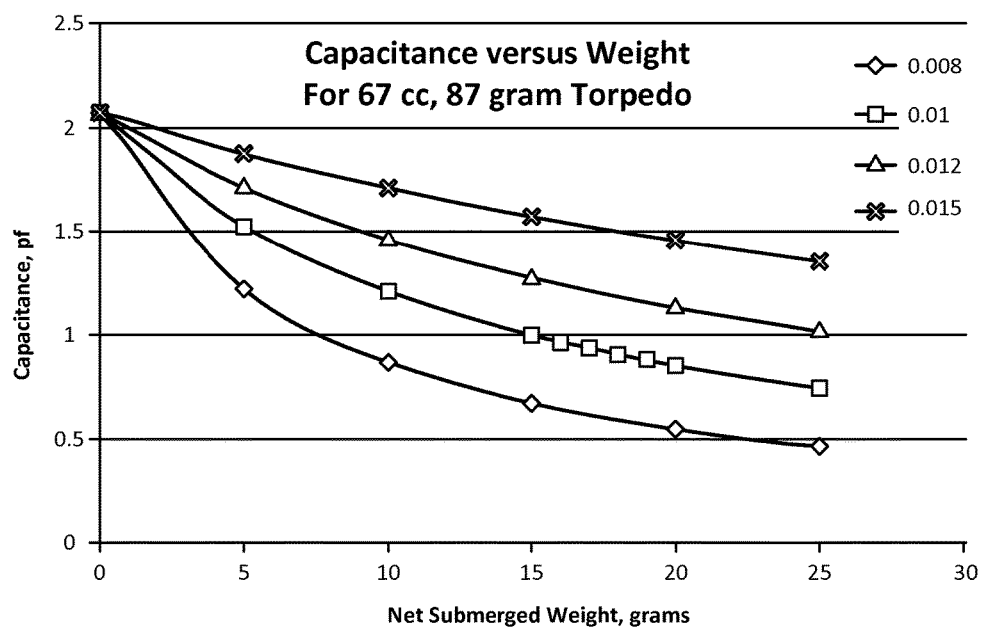
FIG. 16 is a chart showing the capacitance versus weight for a typical beam deflection, according to this invention.

There are many ways in which the deflection can be measured. Optical and eddy current means are well known. The exemplary embodiment for the present invention is to measure the deflection of the sensing beam 108 as the capacitance between the deflecting load beam 113 and a target 152. Performance of the embodiment for which the sensor, S, is 0.35" wide×0.55" long and is spaced 0.020" from the deflecting load beam 113 with no load was calculated for different thicknesses of a deflecting load beam 113 1.23" long and 0.375" wide. FIG. 16 shows a typical variation of capacitance versus submerged torpedo 110 weight for deflecting load beams 113 of the described embodiment but having different thicknesses ranging from 0.008" to 0.015". The capacitance is in the range of 0.25 to 2.5 picofarads and depends on load as illustrated by the graphs in FIG. 16.

Figure 15:
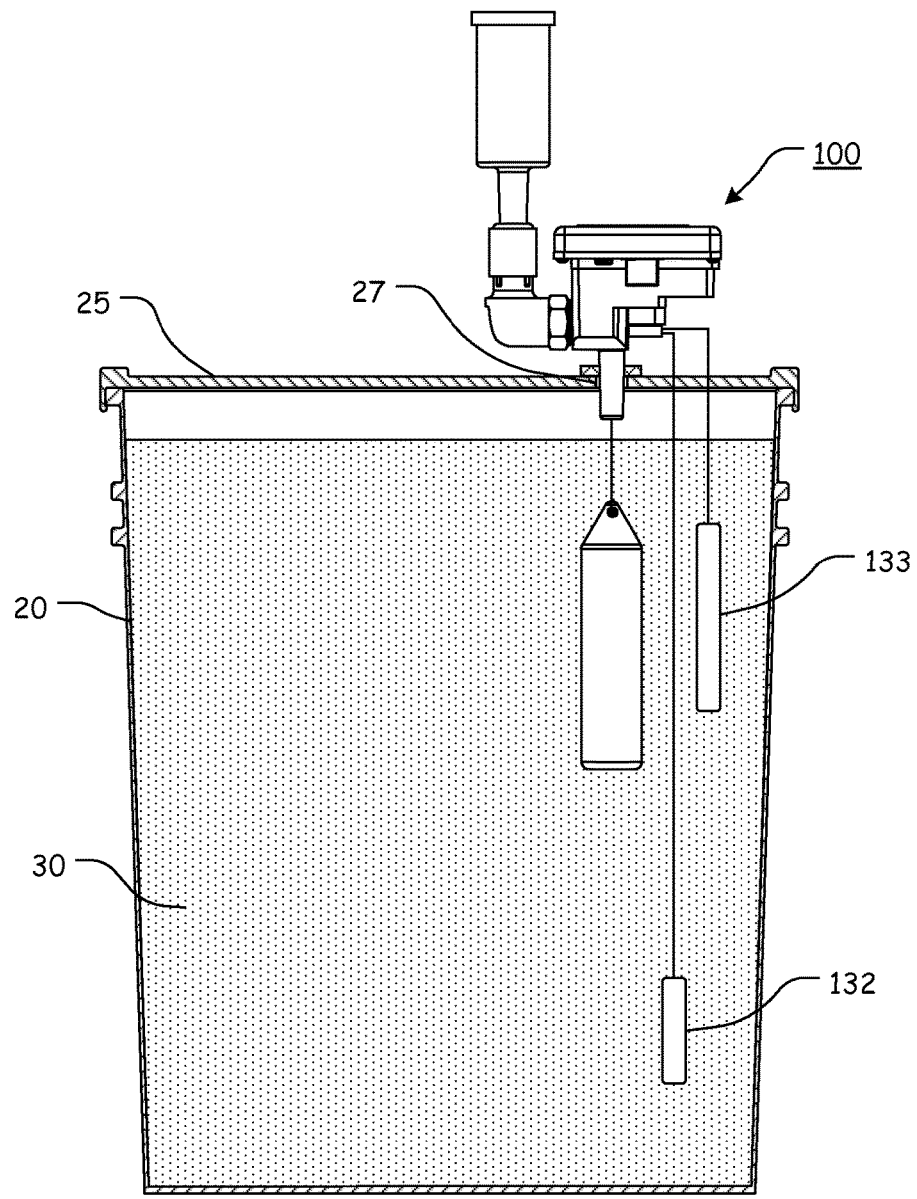
FIG. 15 illustrates a first exemplary embodiment of the density meter installed in an exemplary container to measure the density of a fluid, according to this invention.

FIG. 15 illustrates a first exemplary embodiment of the density meter 100 installed in an exemplary container 20 to measure the density of a fluid 30, according to this invention. As illustrated in FIG. 15, the density meter 100 is installed atop a lid 25 of the container 20. The torpedo 110 is submerged in the fluid 30 and the suspension line 129 and/or at least a portion of the housing 130 is fitted through an aperture 27 in the lid 25.

In various exemplary, nonlimiting embodiments, the density meter 100 also includes at least some of a temperature sensor 132, and an optional heating and/or cooling means 133. In this manner, the systems and methods of the present invention are able to receive current temperature data from the temperature sensor 132, representing a temperature of a fluid. The temperature data is being transmitted to be compared with data representing a desired temperature. If the current temperature is not equal to the desired temperature, the heating and/or cooling means 133 can be controlled so that the temperature of the fluid 30 can be brought to a desired temperature.

In various exemplary, nonlimiting embodiments, data can be transmitted from the density meter 100 via a Bluetooth wireless transmitter, such as, for example, Wireless Wi-Fi 802.11 b/g/n. Depending on end user requirements, device configuration, and usage environment, other wireless communication methods can be employed (e.g., wireless Wi-Fi (IEEE 802.11), Zigbee (IEEE 802.15.4), Bluetooth Low Energy, ANT, and proprietary wireless standards at various frequencies). For example, in one exemplary embodiment a 2.4 GHz, Bluetooth V2.1 radio module is utilized, allowing communication directly to smart phones, computing devices, and tablets that support this Bluetooth protocol. This has the advantage that the density meter 100 can communicate directly with devices with built-in wireless communication capabilities, in this example, via Bluetooth.

Figure 5:
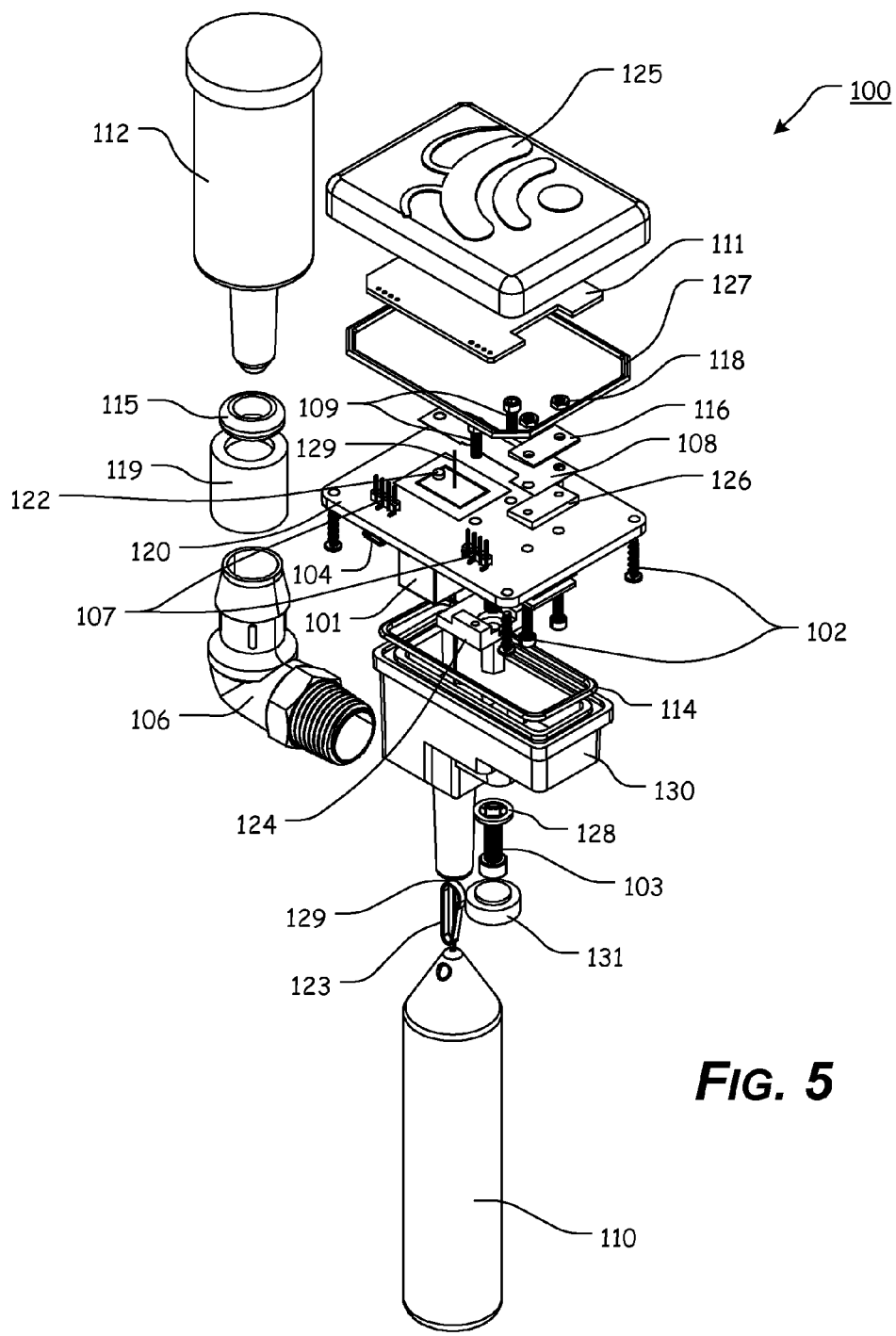
FIG. 5 shows an alternate upper exploded view of the first exemplary embodiment of the density meter, according to this invention.
Figure 6:
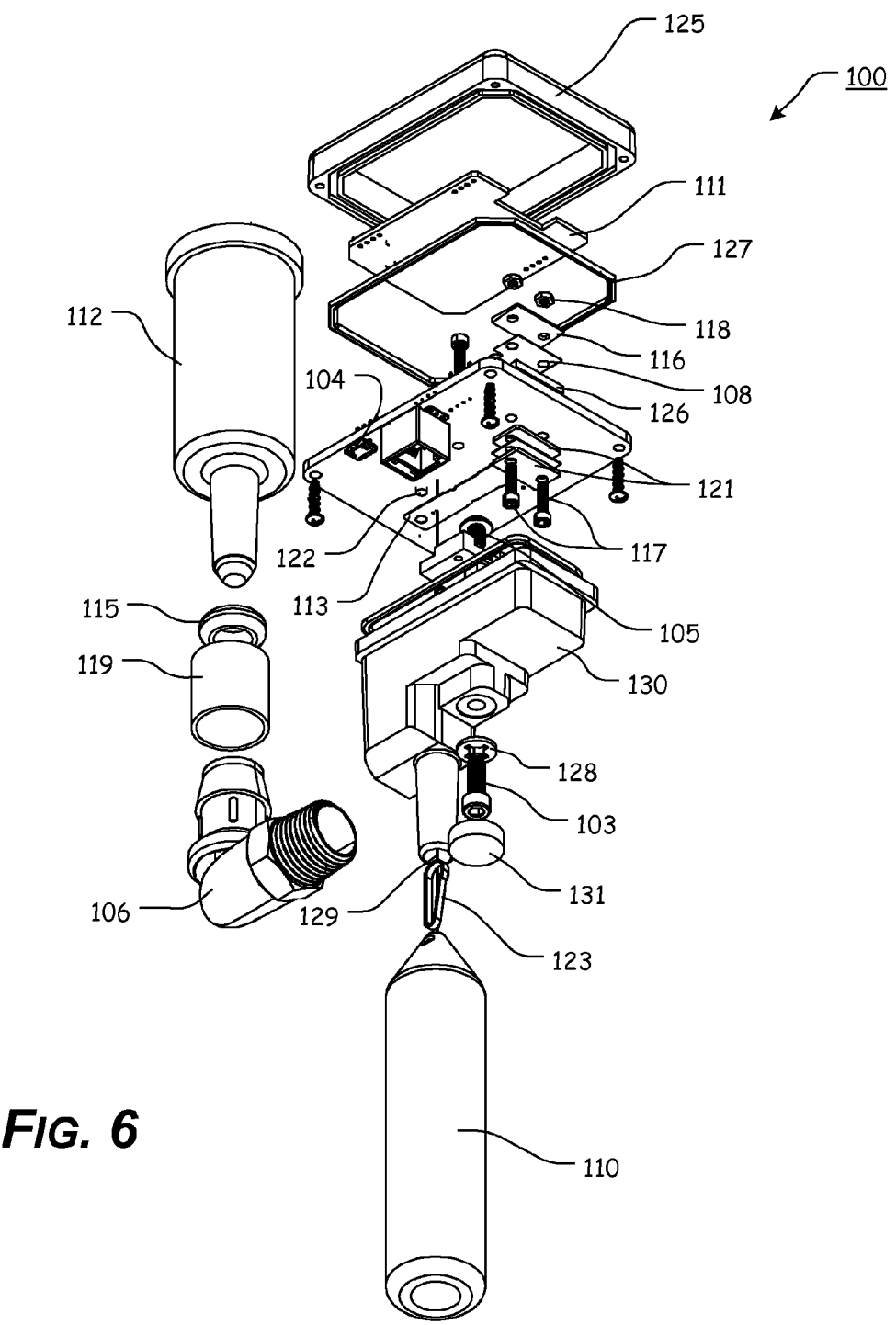
FIG. 6 shows a lower exploded view of the first exemplary embodiment of the density meter, according to this invention.
Figure 7A:
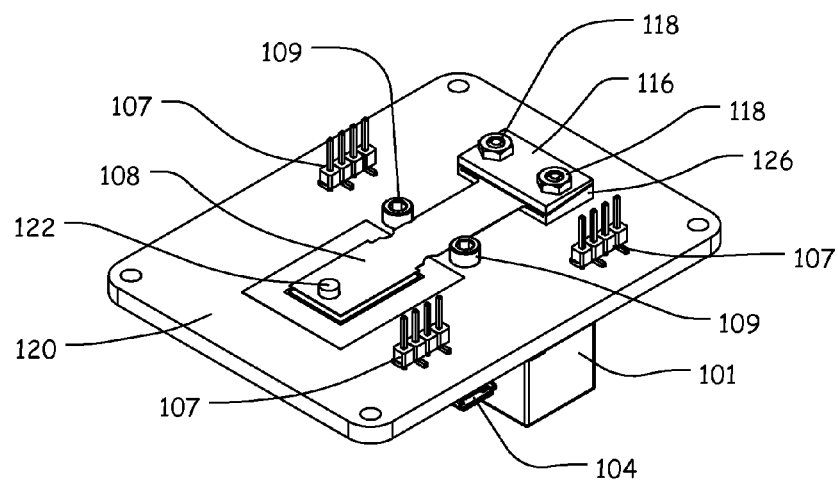
FIG. 7A shows an upper view of a first exemplary embodiment of a printed circuit board of the density meter, according to this invention.
Figure 7B:
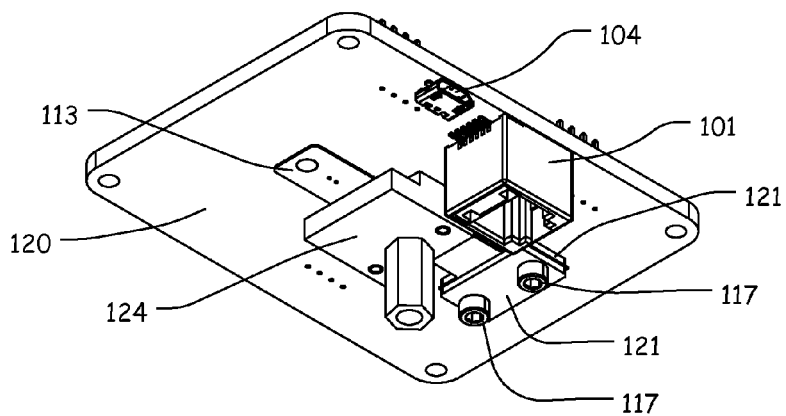
FIG. 7B shows a lower view of the first exemplary embodiment of the printed circuit board of the density meter, according to this invention.
Figure 8A:
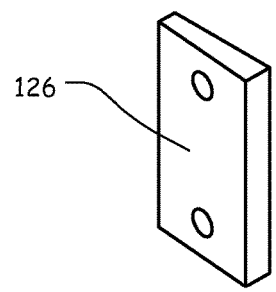
FIG. 8A shows an isometric view of a first exemplary embodiment of a lower wedge of the density meter, according to this invention.
Figure 8B:
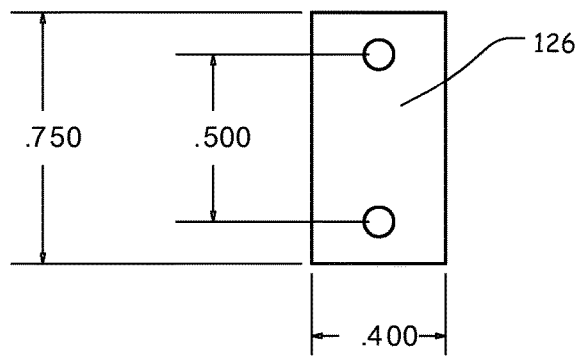
FIG. 8B shows a top view of a first exemplary embodiment of a lower wedge of the density meter, according to this invention.
Figure 8C:
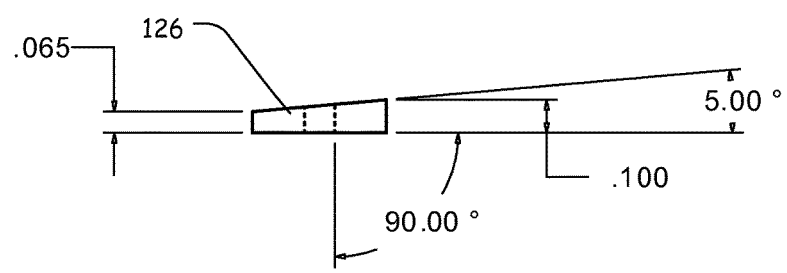
FIG. 8C shows a side view of a first exemplary embodiment of a lower wedge of the density meter, according to this invention.
Figure 9A:
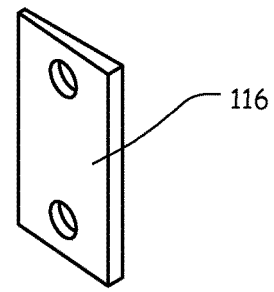
FIG. 9A shows an isometric view of a first exemplary embodiment of an upper wedge of the density meter, according to this invention.
Figure 9B:
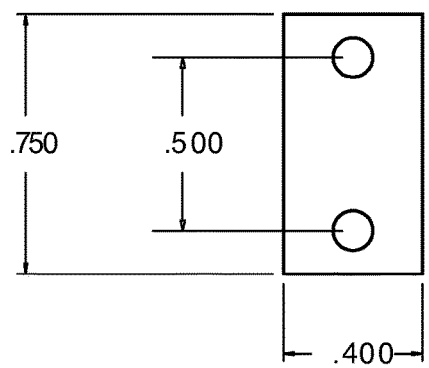
FIG. 9B shows a top view of a first exemplary embodiment of an upper wedge of the density meter, according to this invention.
Figure 9C:
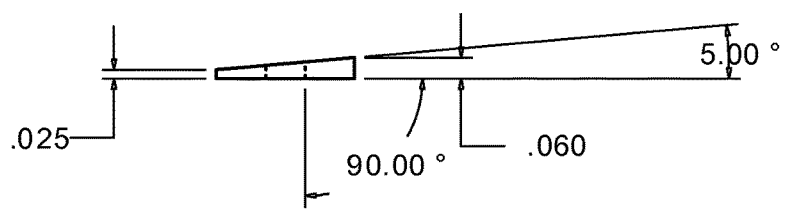
FIG. 9C shows a side view of a first exemplary embodiment of an upper wedge of the density meter, according to this invention.

In addition to sensing capacitance, the electronics described in FIG. 5 measure and transmit temperature data. Data taking and transmissions may be made at any desired rate between about 10 readings per second to very slow, perhaps 3 times per hour or even slower.

In certain exemplary embodiments, the density meter 100 includes an integral readout and built-in calibration tables, formulas, and other suitable reporting scales so the measurements are communicated to the user in a desired format such as "percent alcohol content" for beer fermentation. In addition, the circuits can store, log, display, and/or transmit data to other remote devices, e.g., smart phones, tablets, personal computers, and other devices with computational features.

In some applications for which the density meter 100 is deployed in a location, which blocks wireless transmissions such as a hermetically sealed stainless steel vessel, a repeater antenna may be used to transfer the signals through the wall of the vessel. In another instance, a double-ended antenna may be used to transfer the signal through the wall. Alternatively, a window, which is transparent to the transmission band, may be installed in the wall. In other cases, a wired connection may be made to the hydrometer and data communicated over-the-wire instead of wirelessly. A mounting mechanism in the vessel may serve as either a wired connection or as a repeater antenna for wireless communication.

Typically the density meter 100 is powered by a battery. The battery may be replaceable or rechargeable. Other methods of powering the density meter 100 and or receiver can be incorporated depending on application requirements and usage environment. For example, a super capacitor could store energy gathered from energy harvesting sources such as solar, thermal, vibration, or other energy harvesting device, including power from mains (e.g., 110-120 VAC).

When reporting density, it is important to specify the reference conditions because the density of fluids in general and water in particular depend on temperature and pressure. It is common to use atmospheric pressure and the density of pure water at 4 degrees C. (which is 0.999972 g/cc) or the density of water at 20 degrees C., which is 0.9982071 g/cc.

Figure 17:
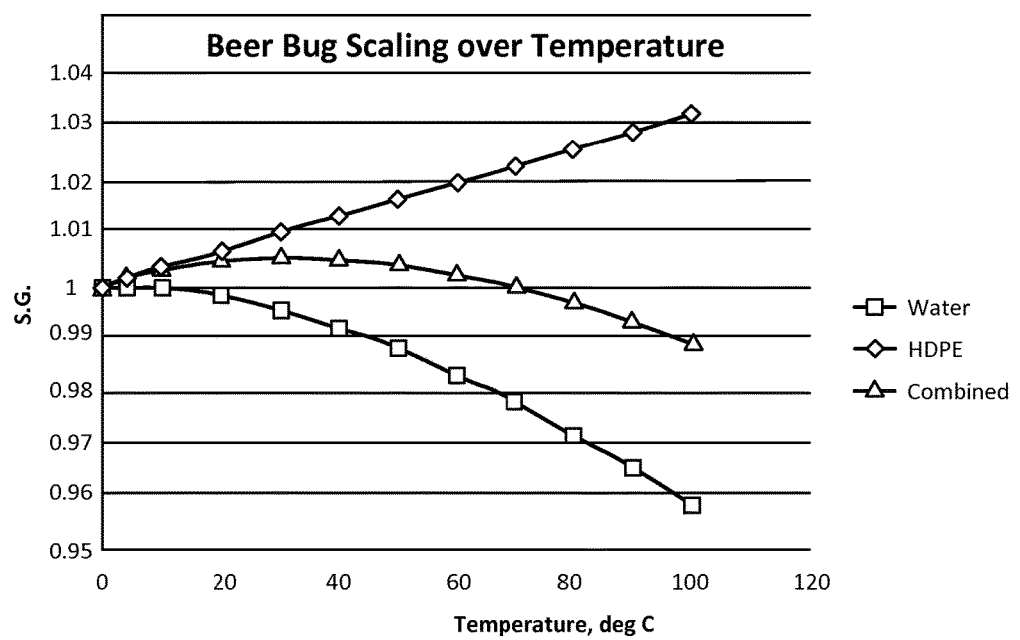
FIG. 17 is a chart showing the density of a torpedo of HDPE versus temperature, according to this invention.

The density of water as a function of temperature is shown as the water curve in FIG. 17. The density of fermenting beer or wine, for example, is assumed to mimic the water curve. To get truly accurate values for the density of beer, we need to either take the sample at a reference temperature or use a curve to convert the reading to the reference condition.

The torpedo 110 of the present invention expands thermally with temperature. The HDPE curve in FIG. 17 assumes a linear thermal expansion coefficient of 108 micrometers/meter/degree C. That is, as the torpedo 110 expands, the buoyancy force acts on a greater volume and it thus appears as if the density of the fluid has increased.

Combining the HDPE curve and water curves, one obtains the combined HDPE and water curve in FIG. 17. In the region of greatest interest from 15-40 degrees C., the uncompensated density measured with a torpedo 110 is within 0.0015 of the density, which would be measured if the sample were heated or cooled to a reference temperature.

Figure 18:
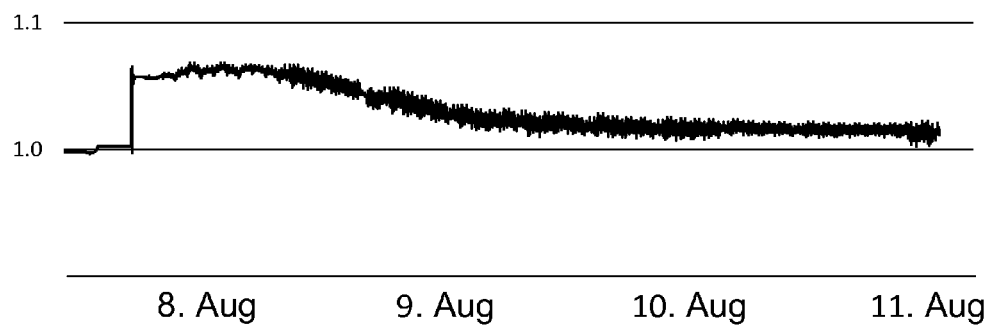
FIG. 18 shows an instance of density during the fermentation of beer, according to this invention.

FIG. 18 shows a typical measurement of the density of a fermenting beer over a several day period. The current embodiment of the invention is such that the specific gravity and temperature measurements are transmitted at regular intervals to a remote computation facility in the cloud or at some other location. This allows real-time processing of the derived products. The term "derived products", as used herein, includes but is not limited to: filtering, spectral decomposition (using Fourier, wavelet, or other analyses), correlation, differentiation, integration, thresholding, reasonableness checks, and dropout and spike corrections.

Also included in the current embodiment is the ability to use these measurements and their derived products in active or passive feedback control of sensors and actuators located in and/or around the fluid 30. One example may be feedback of the density and temperature measurements an/or the derived products to actively control the temperature of the fluid 30 to control the density change of the fermentation fluid 30 to a specific profile.

Figure 19:
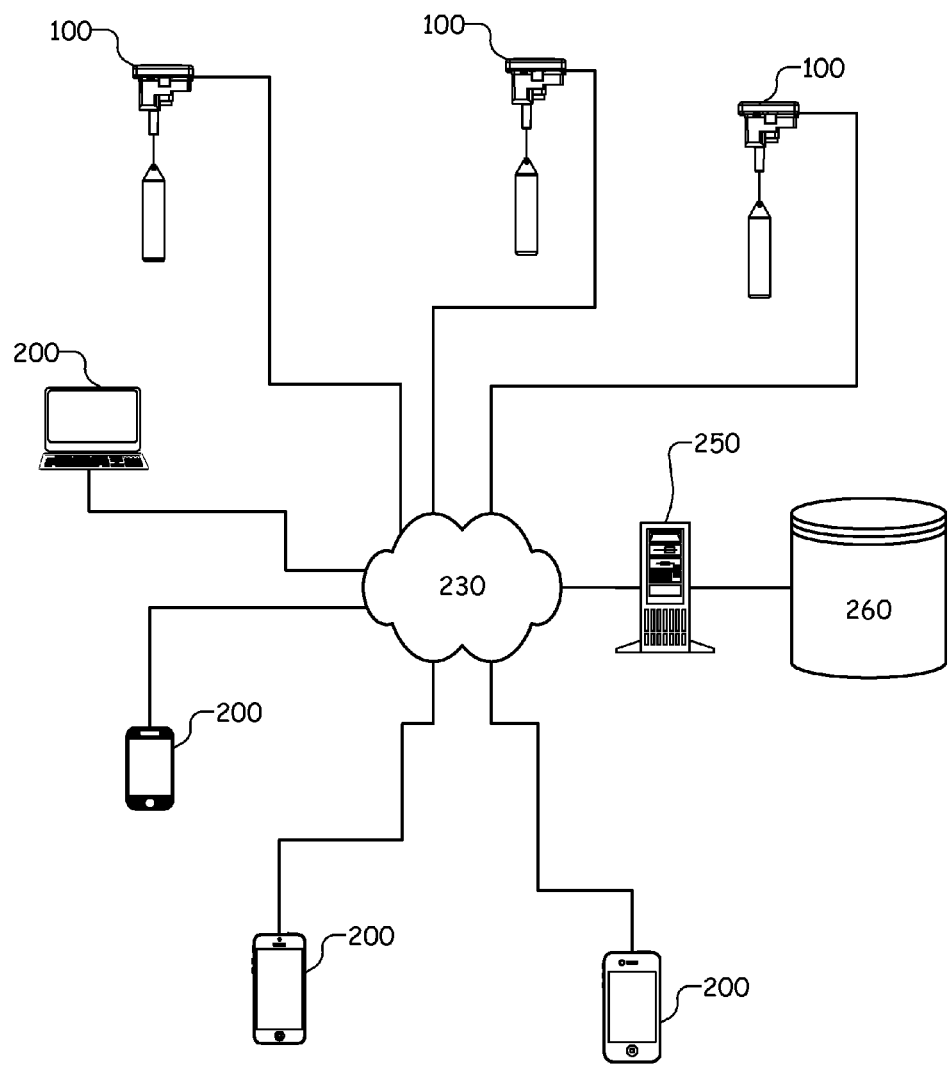
FIG. 19 shows a functional block diagram outlining an exemplary embodiment of the exemplary systems and apparatuses of the BeerBug™ App, according to this invention.

FIG. 19 shows a functional block diagram outlining an exemplary embodiment of the exemplary systems and apparatuses of the BeerBug™ App, according to this invention. In illustrative, non-limiting embodiment(s) of this invention, the BeerBug™ App relies on several components. For example, the present invention utilizes at least some of at least one density meter 100 providing real-time or near real-time density data, a server 250 to receive the density data, a database 260 to store density data, and at least client device 200 to retrieve density data, filtered density data, or information relating to or derived from the density data.

As shown in FIG. 19, the BeerBug™ App includes at least some of at least one client device 200, at least one density meter 100, and a server 250. In various exemplary embodiments, the BeerBug™ App includes a plurality of client devices 200. Each client device 200 is linked, either directly or indirectly, to a distributed network 230, and, in turn, to the server 250.

In various exemplary embodiments, the distributed network 230 is, for example, an intranet, an extranet, the Internet and, more particularly, the World Wide Web portion of the Internet, a Local Area Network (LAN), a Wide Area Network (WAN), or any other presently known or later developed distributed network 230. It should be appreciated that, in various exemplary embodiments, the distributed network 230 may be, for example, a particular node, such as, for example, a specific web page, of a larger distributed network 230.

In various exemplary embodiments, each of the client devices 200 is typically a smart phone, having a memory containing communications software and some form of Internet connectivity, such as a cellular data connection, a Wi-Fi connection, or the like. The Internet connector may be used with the communications software for communication, via the distributed network 230, to the server 250.

It should be understood that at least one of the client devices 200 may be a Network Computer, a smart phone, a tablet, a personal digital assistant (PDA), a handheld organizer, or a similar or hybrid electronic device.

In various exemplary embodiments, each of the client devices 200 also includes a display and one or more input devices. In various exemplary embodiments, the display may be any other known or later developed system capable of displaying data. The one or more input devices may be one or more of a keyboard, a mouse, a touch screen, a touch pad, a stylus, a microphone, a camera, or any other known or later developed device capable of inputting data into the client device 200.

Each of the client devices 200 also includes memory to store data, a processor to convert data to text and/or symbolic graphics, and a screen to display the text and/or symbolic graphics.

In various exemplary embodiments, the server 250 is capable of maintaining density, temperature measurement, and/or other data, discreet user data, and other information, and transmitting such data and information, via the network 230, to an appropriate client device 200.

It should be appreciated that the server 250 may optionally utilize sufficient security methods to ensure safe storage and integrity of data and information.

The server 250 is connected, via one or more linked connections, to at least some of a database 260.

The database 260 includes various suitable software programs and memory for storing and/or updating a plurality of discreet user and density records, data, and/or information. In various exemplary embodiments, the records, data, and/or information contained within the database 260 comprise both static information (such as prior density information) and dynamic information (such as current or updated density information).

It should be appreciated that the type and level of dynamic information in the database 260 may vary and may be updated periodically, as appropriate or necessary. The dynamic information is updated via input from each discreet user's density meter 100. Data including real-time or near real-time density information is passed over the network 230.

In various exemplary embodiments, the database 260 and/or any other accessible database (not shown) stores software and data used by the BeerBug™ App. The server 250 manages reading data from and writing data to the database 260 and or any other accessible database 260 (not shown). The server 250 also drives the transmission of data to and the reception of data from each of the client devices 200. The server 250 also performs real-time processing of the measurements (derived products) to include but not limited to: filtering, spectral decomposition (using Fourier, wavelet, or other analyses), correlation, differentiation, integration, thresholding, reasonableness checks, and dropout and spike corrections.

Thus, in various exemplary embodiments, each of the client devices 200 is able to access, store, retrieve, and process information from any one or more of the database 260, the distributed network 230, or any other accessible database (not shown). In this manner, it is not essential that any particular information be stored in the database 260. Alternatively, this information can be stored in, for example, the server 250, one or more of the client devices 200, and/or the distributed network 230. The client device 200 may also perform real-time processing of the measurements (derived products) to include but not limited to: filtering, spectral decomposition (using Fourier, wavelet, or other analyses), correlation, differentiation, integration, thresholding, reasonableness checks, and dropout and spike corrections.

In various exemplary embodiments, the BeerBug™ App will include software executing on the server 250. It should be appreciated that any other known or later developed system capable of processing and outputting data could be used in place of the server 250.

In the various exemplary embodiments described herein, each of the client devices 200 and the server 250 interface, for example, with the network 230, via a linked connection. Likewise, the database 260 interfaces with the network 230, via a linked connection.

The linked connection(s) may be any known or later developed device or system for connecting any of the client devices 200, the server 250, the database 260, and/or the network 230, including a direct wired connection, a connection over a LAN, a WAN, or any other distributed network, a connection over the public switched telephone network, a connection over a Wi-Fi connection, a connection over a cellular telephone network, a satellite connection or the like. In general, the linked connections may be any known or later developed connection system or structure usable to connect any of the client devices 200, the server 250, the database 260, and/or the network 230, including both wired and wireless connections.

Figure 20:
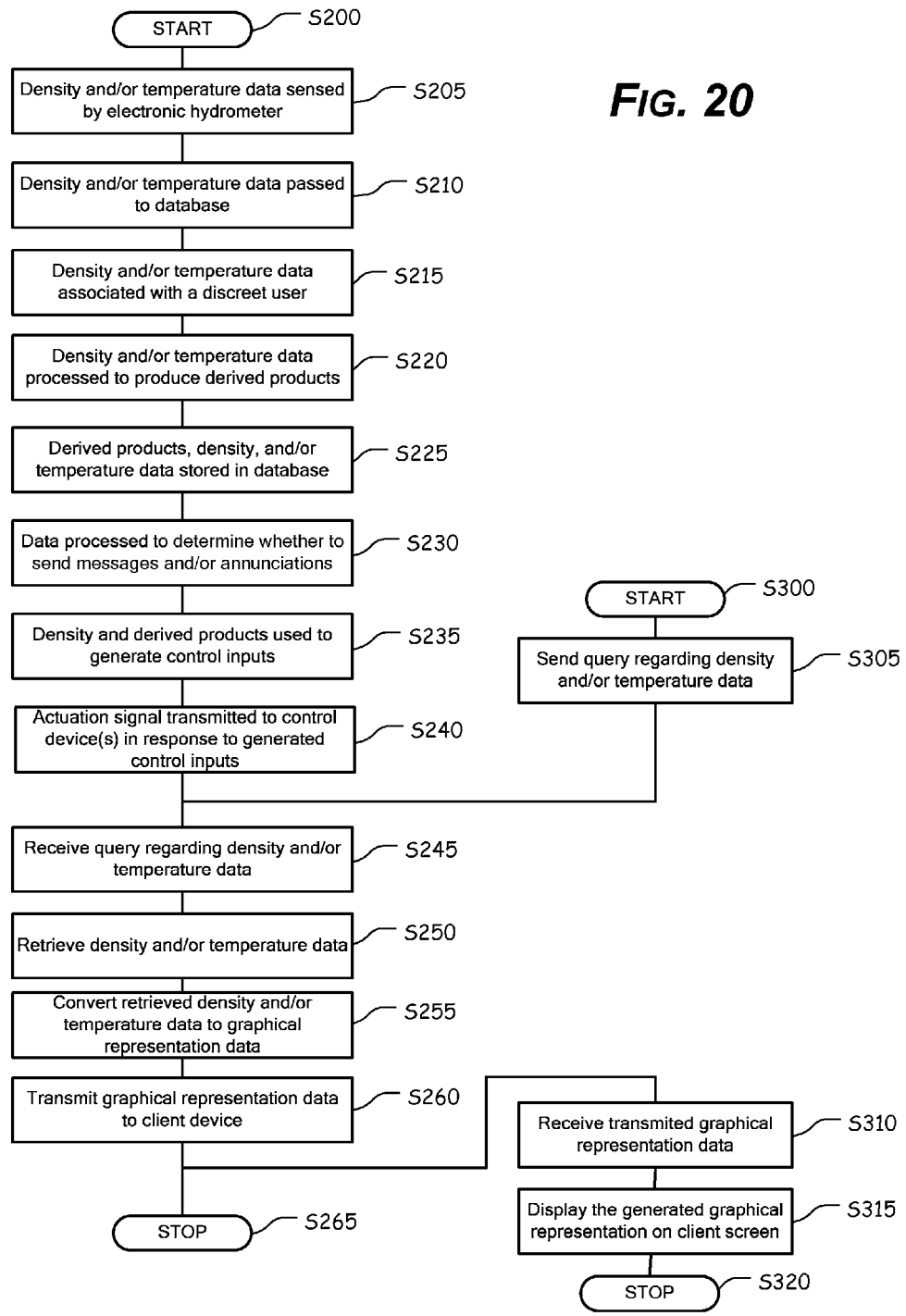
FIG. 20 shows a flowchart outlining an exemplary embodiment of a method utilized by the BeerBug™ App, according to this invention.

FIG. 20 shows a flowchart outlining one exemplary embodiment of a method for displaying a graphical representation of density information relating to a fluid 30 on a user's or client's screen, according to this invention.

As shown in FIG. 20, beginning in step S200, the method begins and control continues to step S205, wherein at least some density and optional temperature data or other information is sensed by a density meter 100.

Once sensed, control continues to step S210 and the density and optional temperature data is passed, via the density meter 100, over the network 230, to the server 250, to be associated with a discreet user and stored in the database 260. In various exemplary embodiments, at least some temperature data is also sensed in step S205, via the density meter 100, and passed along with the density data in step S210.

Next, in step S215, the density data and optional temperature data are associated with a discreet user. In various exemplary, nonlimiting embodiments, the discreet user is a specifically identified batch associated with a discreet user. Then, in step S220, the density data and/or the optional temperature data can be normalized to produce specific gravity, or otherwise processed to produce derived products to include, but not limited to: filtering, spectral decomposition (using Fourier, wavelet, or other analyses), correlation, differentiation, integration, thresholding, reasonableness checks, and dropout and spike corrections from the density data and optional filter temperature data.

Once the density data and optional temperature data are associated with the discreet user and filtered, the method advances to step S225 and the derived products and density data and optional temperature data are stored within the database 260.

In various exemplary, nonlimiting embodiments, the BeerBug™ App utilizes a density filtering algorithm to produce filtered density data and optional filtered temperature data.

Once stored within the database 260, the filtered density data and optional filtered temperature data can be queried by the client software resident on one or more of the client devices 200, via the network 230, such that the filtered density data and optional filtered temperature data can be transmitted to the client software, in response to the query.

Then, in step S230, logic will process derived products and density data and optional temperature data using logic and thresholding to decide whether any real-time messages and/or annunciations should be sent to the client device 200. Such messages or warnings may pertain (but are not limited to) to the stage of the fermentation, abnormalities in the process, the need for action on the part of a user. Messages may be (but are not limited to) graphical, textual, aural, vibratory, or other sensory.

Next, in step S235, the density and its derived products are used as the basis for generating manual or automatic control inputs to directly or indirectly control the density and/or temperature of the fluid through manual or automatic control means.

Control then advances to step S240, and an actuation signal is transmitted to a control device or devices in response to the generated manual or automatic control inputs.

Beginning in step S300, if a discreet user submits a query regarding density data and/or temperature data or derived products, the method begins and control continues to step S305, wherein a query is sent requesting the filtered density data and optional filtered temperature data.

In response to a query in step S305 from a client device 200, the method advances to step S245, wherein the request for the derived products and density data and optional filter temperature data is received. Then, in step S250, the derived products and density data and optional filtered temperature data for the discreet user is retrieved from the database 260 and control continues to step S255 wherein the retrieved data is converted into a graphical representation data that can be displayed on the client device 200 screen.

Then, in step S260, the graphical representation data is transmitted, via the server 250 and the distributed network 230, to the client device 200. Once the graphical representation data has been transmitted, the method may optionally return to step S205, wherein at least some updated density data or other information is sensed by a density meter 100 and the method continues. Alternatively, once the graphical representation data has been transmitted, control may optionally jump to step S265 and the method ends.

Once the graphical representation data is transmitted in step S260, the method advances to step S310, wherein the transmitted graphical representation data is received by the client device 280. Then, in step S315, the received graphical representation data is displayed on the client device 200 screen.

Once the graphical representation data has been displayed on the client device 200, the method may optionally return to step S310, wherein at least some transmitted updated graphical representation data is received by the client device 280 and the method continues. Alternatively, once the graphical representation data has been displayed on the client device 200, control may optionally jump to step S320 and the method ends.

Figure 21:
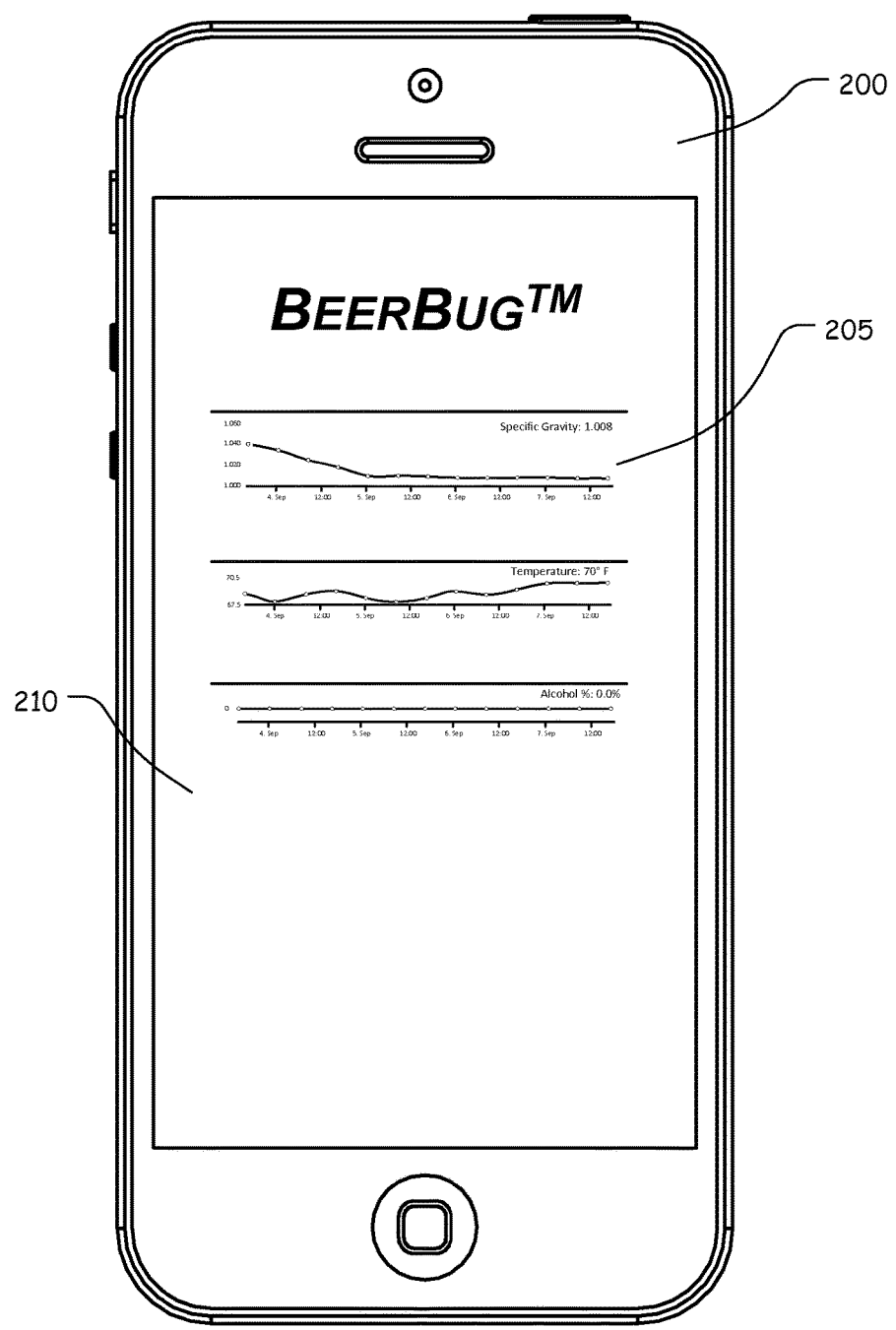
FIG. 21 illustrates a first exemplary embodiment of a graphical display presented to a user using the systems, methods, and apparatuses of the BeerBug™ App, according to this invention.
Figure 22:
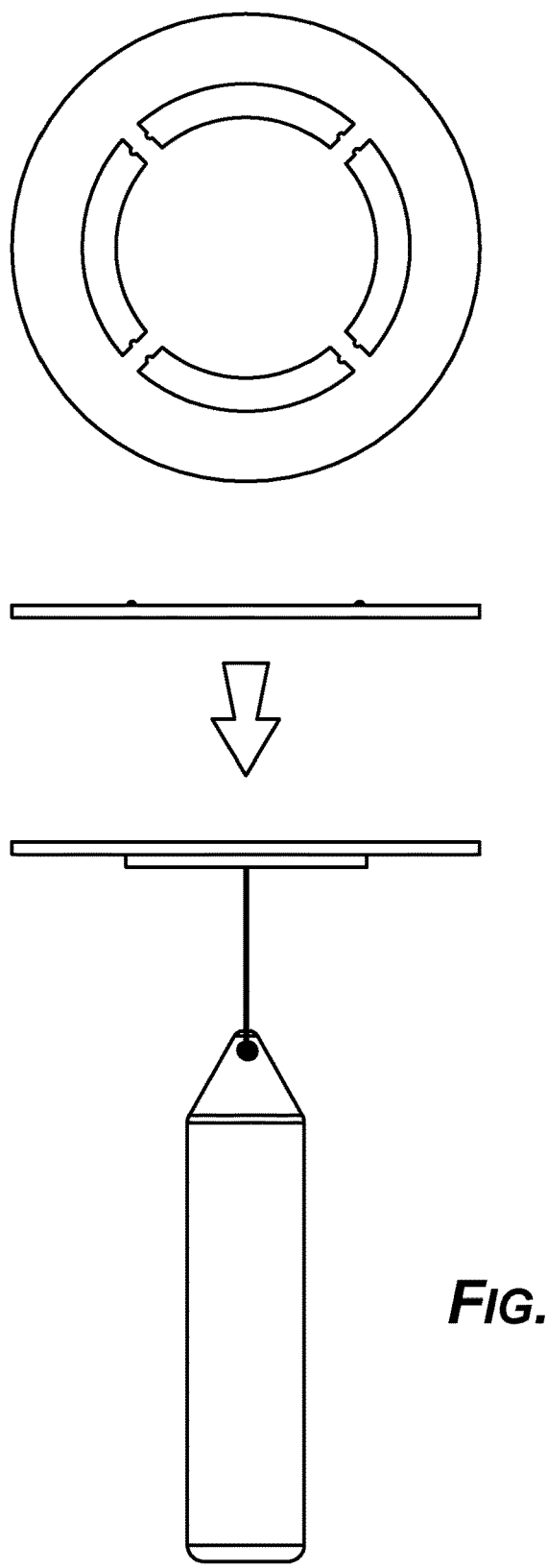
FIG. 22 illustrates an exemplary embodiment of a spring element comprising a circular spring, according to this invention.
Figure 23:
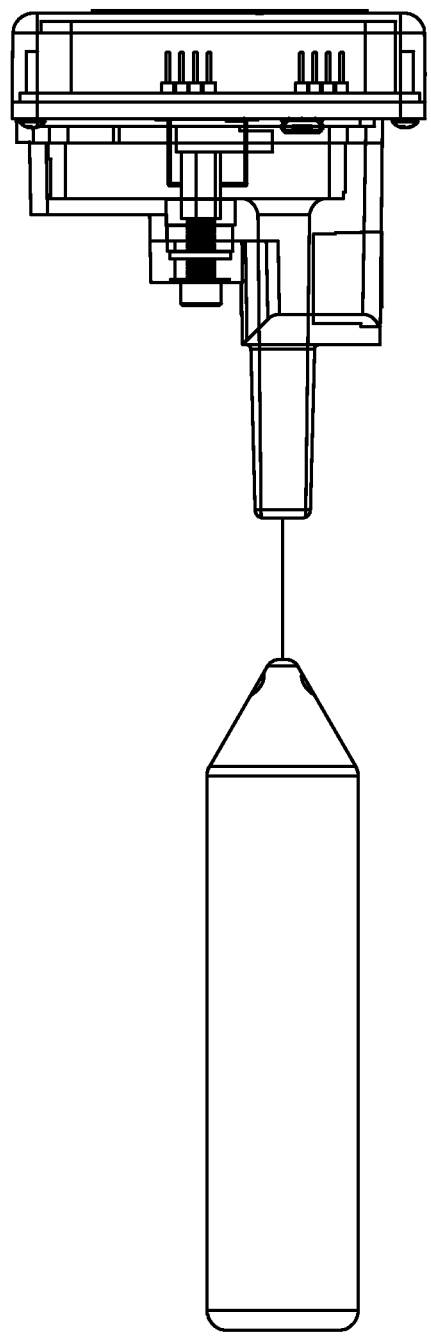
FIG. 23 illustrates an exemplary embodiment of an eddy current embodiment of the density meter, according to this invention.
Figure 24:
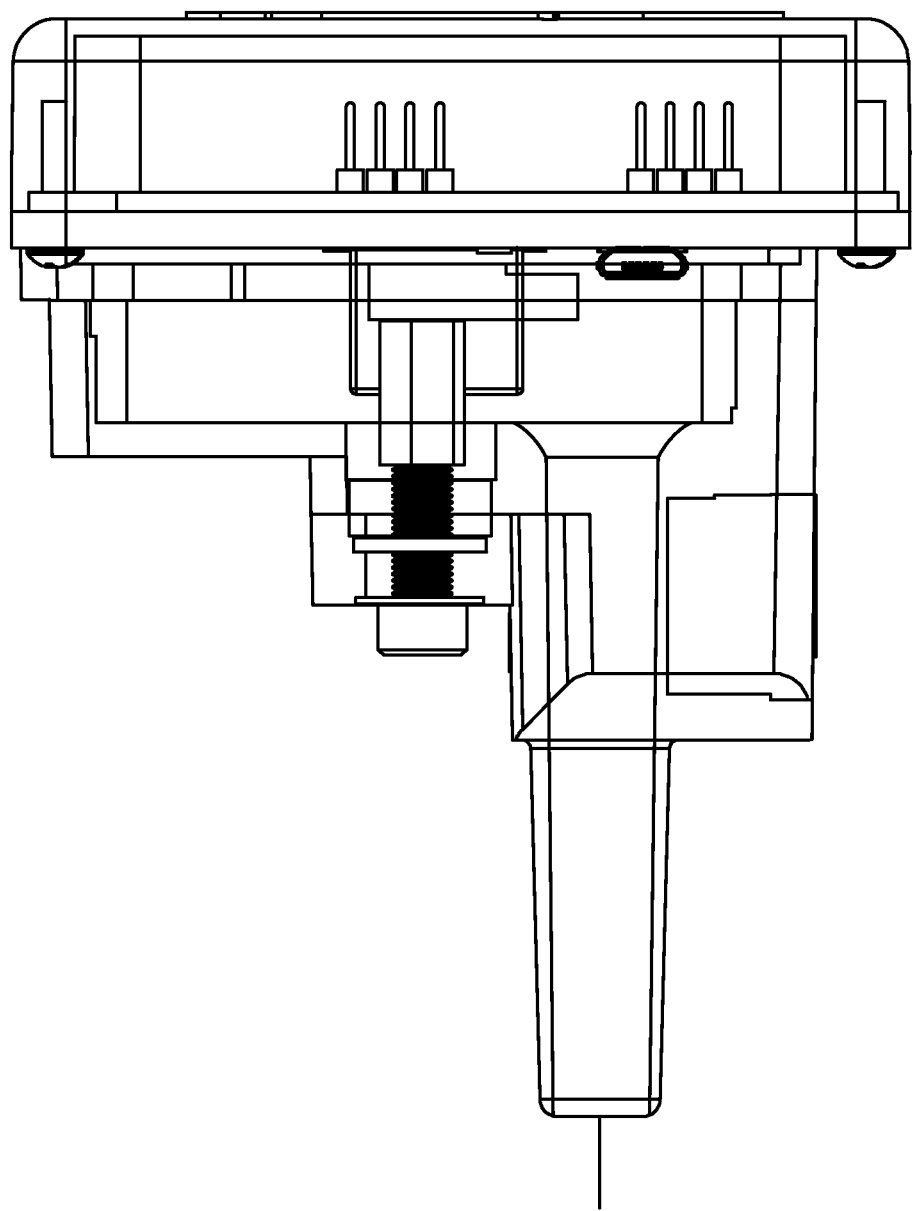
FIG. 24 illustrates first sectional view of an exemplary embodiment of an eddy current embodiment of the density meter, according to this invention.
Figure 25:
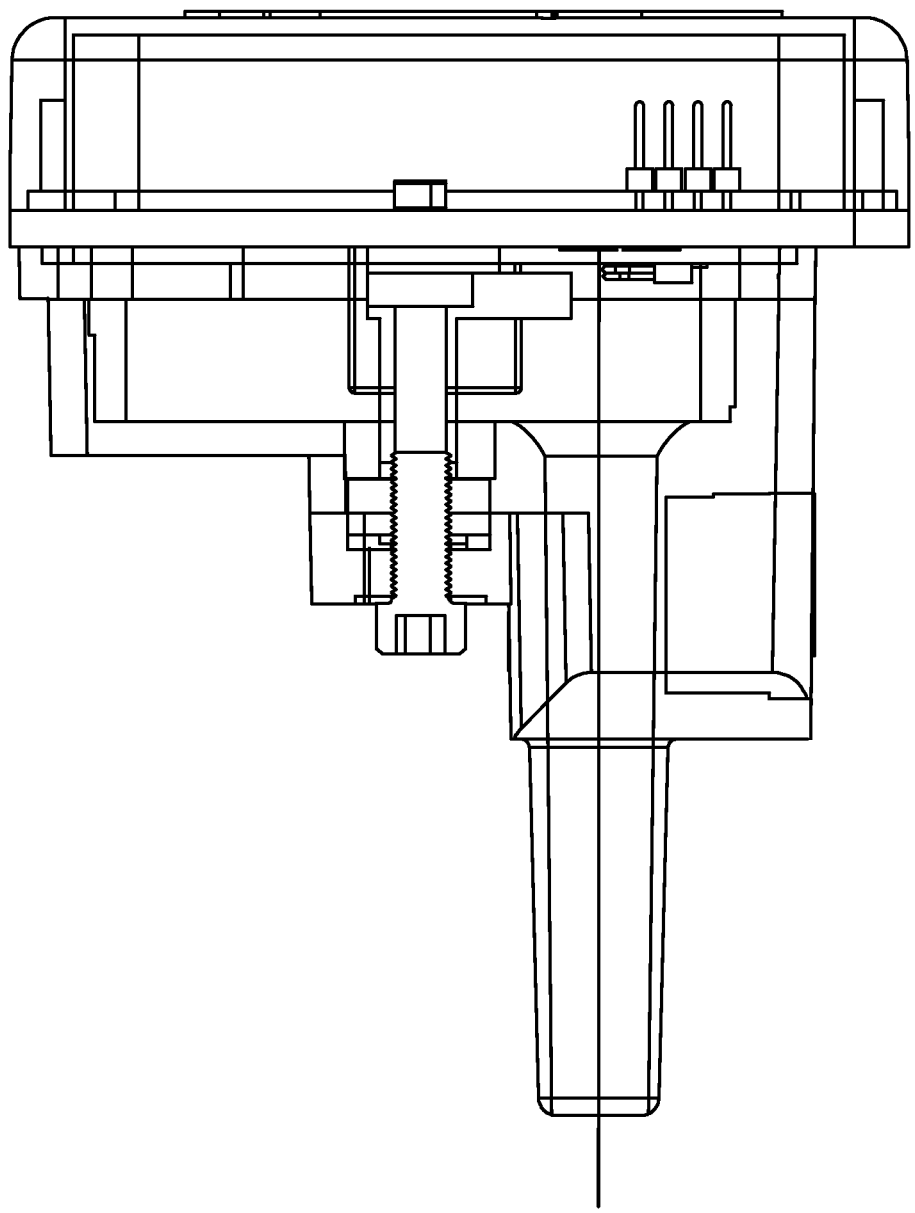
FIG. 25 illustrates second sectional view of an exemplary embodiment of an eddy current embodiment of the density meter, according to this invention.
Figure 26:
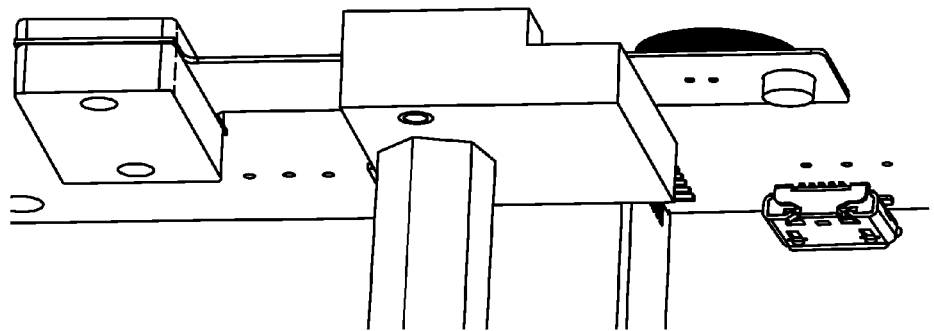
FIG. 26 illustrates an exemplary embodiment of an isoplanar coil and target, according to this invention.
Figure 27:
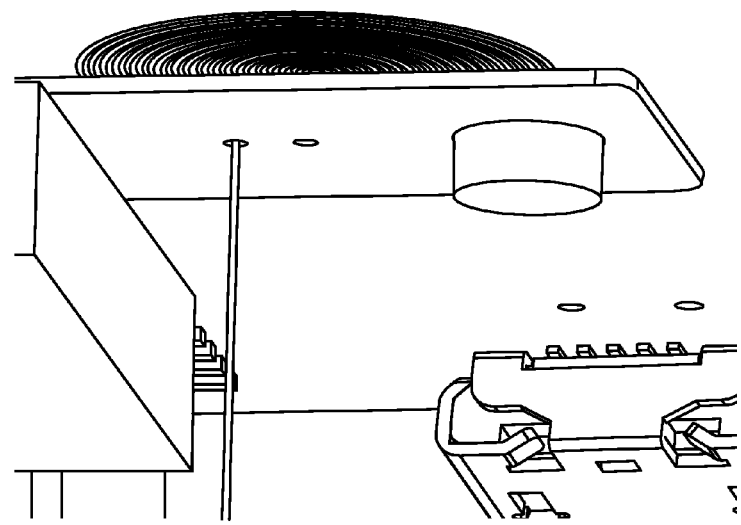
FIG. 27 illustrates more detailed, sectional view of an exemplary embodiment of an isoplanar coil and target, according to this invention.
Figure 28:
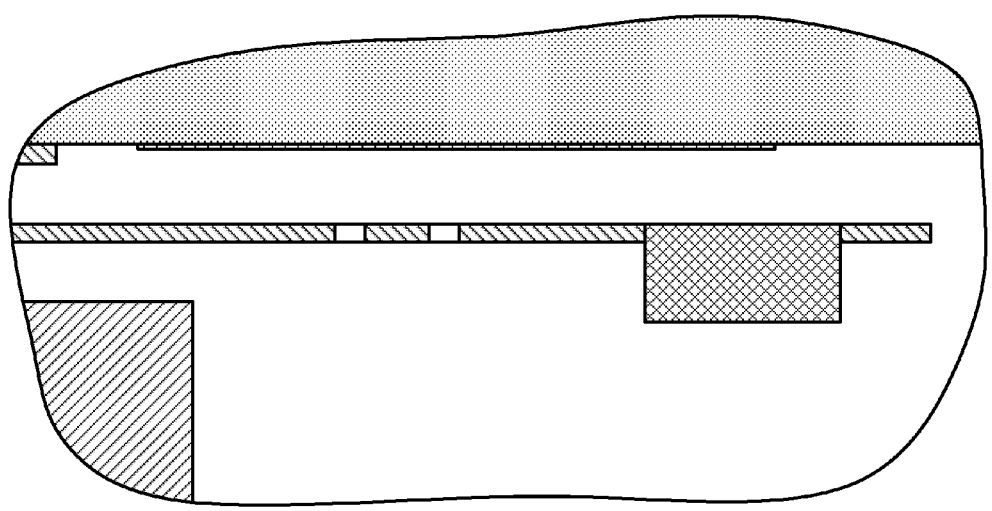
FIG. 28 illustrates a more detailed view of an exemplary embodiment of an isoplanar coil and target, according to this invention.

As shown in FIG. 21, the BeerBug™ App of the present invention is able to present graphical representations 205 of density and/or temperature information that are displayed in a particular ornamental design on a screen 210 of a client device 200 in an easily discernible format.

Client device 200 may also be able to display or react to any real-time messages and/or annunciations should be sent to the client device 200 from the database 260 or server 250. Such messages or warnings may pertain (but are not limited to) to the stage of the fermentation, abnormalities in the process, the need for action on the part of the user. Messages may be (but are not limited to) graphical, textual, aural, vibratory, or other sensory.

It should also be appreciated that a more detailed explanation of the specific tools and/or methods used to incorporate the features and elements of the present invention into an application, further instructions regarding how to operate and/or use the BeerBug™ App, and certain other items and/or techniques necessary for the implementation and/or operation of the various exemplary embodiments of the present invention are not provided herein because such background information will be known to one of ordinary skill in the art. Therefore, it is believed that the level of description provided herein is sufficient to enable one of ordinary skill in the art to understand and practice the systems, methods, and apparatuses of the present invention, as described.

While this invention has been described in conjunction with the exemplary embodiments outlined above, the foregoing description of exemplary embodiments of the invention, as set forth above, are intended to be illustrative, not limiting and the fundamental invention should not be considered to be necessarily so constrained. It is evident that the invention is not limited to the particular variation set forth and many alternatives, adaptations modifications, and/or variations will be apparent to those skilled in the art.

Furthermore, where a range of values is provided, it is understood that every intervening value, between the upper and lower limit of that range and any other stated or intervening value in that stated range is encompassed within the invention. The upper and lower limits of these smaller ranges may independently be included in the smaller ranges and is also encompassed within the invention, subject to any specifically excluded limit in the stated range. Where the stated range includes one or both of the limits, ranges excluding either or both of those included limits are also included in the invention.

It is to be understood that the phraseology of terminology employed herein is for the purpose of description and not of limitation. Unless defined otherwise, all technical and scientific terms used herein have the same meaning as commonly understood by one of ordinary skill in the art to which this invention belongs.

In addition, it is contemplated that any optional feature of the inventive variations described herein may be set forth and claimed independently, or in combination with any one or more of the features described herein.

Accordingly, the foregoing description of exemplary embodiments will reveal the general nature of the invention, such that others may, by applying current knowledge, change, vary, modify, and/or adapt these exemplary, non-limiting embodiments for various applications without departing from the spirit and scope of the invention and elements or methods similar or equivalent to those described herein can be used in practicing the present invention. Any and all such changes, variations, modifications, and/or adaptations should and are intended to be comprehended within the meaning and range of equivalents of the disclosed exemplary embodiments and may be substituted without departing from the true spirit and scope of the invention.

Also, it is noted that as used herein and in the appended claims, the singular forms "a", "and", "said", and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely", "only", and the like in connection with the recitation of claim elements or the use of a "negative" claim limitation(s).

What is claimed is:

1. A density meter for measuring a density of a fluid, comprising:
   a base plate, wherein a spring element is clamped to said base plate;
   a torpedo, wherein said torpedo comprises a known weight, and wherein said torpedo is attached or coupled to said spring element; and
   a sensor, wherein said sensor measures a deflection of said spring element, as said torpedo displaces a volume of a fluid, wherein said spring element is a deflecting load beam and wherein said sensor measures said deflection of said deflecting load beam by measuring said capacitance between said sensor and said deflecting load beam.

2. The density meter of claim 1, wherein said spring element is a cantilever beam.

3. The density meter of claim 1, wherein said spring element is a deflecting load beam and wherein said sensor measures said deflection of said deflecting load beam by measuring induced eddy currents in said deflecting load beam.

4. The density meter of claim 1, further comprising a sensing beam, wherein said deflecting load beam is coupled to said sensing beam such that movement of said deflecting load beam is coupled to movement of said sensing beam, and wherein a sensing electrode measures a capacitance between said sensing beam and one or more sensing electrodes.

5. The density meter of claim 4, wherein said deflecting load beam and said sensing beam are coupled magnetically.

6. The density meter of claim 4, wherein said sensor measures said deflection of said sensing beam by measuring induced eddy currents in said sensing beam.

7. The density meter of claim 1, further comprising a transmitter/receiver for transmitting and receiving data.

8. The density meter of claim 1, further comprising software for portable device and/or web-based data storage.

9. The density meter of claim 8, wherein said software processes density and temperature measurements from said density meter in real-time to calculate various derived products.

10. The density meter of claim 9, wherein said various derived products include one or more of filtering, spectral decomposition using Fourier or wavelet analyses, correlation, differentiation, integration, thresholding, reasonableness checks, and dropout and spike corrections.

11. The density meter of claim 10, wherein said density and temperature measurements and derived products are used to generate and send annunciation messages, via an Internet connection.

12. The density meter of claim 10, wherein said density and temperature derived products are used to control density and said derived products of a fluid in real-time.

13. A method for displaying density data and derived products, comprising:
   collecting density data and temperature measurements from a density meter, wherein said density meter comprises:
   a base plate, wherein a spring element is clamped to said base plate;
   a torpedo, wherein said torpedo comprises a known weight, and wherein said torpedo is attached or coupled to said spring element; and
   a sensor, wherein said sensor measures a deflection of said spring element, as said torpedo displaces a volume of a fluid, wherein said spring element is a deflecting load beam and wherein said sensor measures said deflection of said deflecting load beam by measuring said capacitance between said sensor and said deflecting load beam;
   calculating said derived products, including one or more of filtering, spectral decomposition using Fourier or wavelet analyses, correlation, differentiation, integration, thresholding, reasonableness checks, and dropout and spike corrections;
   using said density data, said temperature measurements, and said derived products to generate and send annunciation messages, via an Internet connection, or to control density data and said derived products of a fluid;
   associating said collected density data and temperature measurements with one or more discreet users;
   receiving a query regarding density from a client device associated with a discreet user;
   retrieving, in response to said query, density data associated with said discreet user;
   converting said density data into a graphical representation;
   transmitting said graphical representation associated with said query to said client device associated with said discreet user;
   controlling said transmitted graphical representation to be received by said client device associated with said discreet user; and
   controlling said client device associated with said discreet user to display said graphical representation.

14. A density meter for measuring a density of a fluid, comprising:

a base plate, wherein a spring element is clamped to said base plate, wherein said spring element is a deflecting load beam;

a torpedo, wherein said torpedo comprises a known weight, and wherein said torpedo is attached or coupled to said spring element;

a sensor, wherein said sensor measures a deflection of said spring element by measuring a capacitance between said sensor and said spring element, as said torpedo displaces a volume of said fluid; and software for portable device and/or web-based data storage;

wherein said software processes density data and temperature measurements from said density meter in real-time to calculate various derived products;

wherein said various derived products include one or more of filtering, spectral decomposition using Fourier or wavelet analyses, correlation, differentiation, integration, thresholding, reasonableness checks, and dropout and spike corrections; and wherein said software uses said density data, temperature measurements, and derived products to generate and send annunciation messages, via an Internet connection, or to control density and said derived products of said fluid in real-time by open or closed feedback of density data and temperature measurements.

15. The density meter of claim 14, wherein said spring element is a cantilever beam.

16. The density meter of claim 14, wherein said spring element is a deflecting load beam and wherein said sensor measures said deflection of said deflecting load beam by measuring induced eddy currents in said deflecting load beam.

17. The density meter of claim 14, further comprising a sensing beam, wherein said spring element is a deflecting load beam, wherein said deflecting load beam is coupled to said sensing beam such that movement of said deflecting load beam is coupled to movement of said sensing beam, and wherein a sensing electrode measures a capacitance between said sensing beam and one or more sensing electrodes.

18. The density meter of claim 17, wherein said deflecting load beam and said sensing beam are coupled magnetically.

19. The density meter of claim 14, further comprising a transmitter/receiver for transmitting and receiving data.

* * * * *